(12) United States Patent
Blaesi et al.

(10) Patent No.: US 11,129,798 B2
(45) Date of Patent: Sep. 28, 2021

(54) FIBROUS DOSAGE FORM

(71) Applicant: Aron H. Blaesi, Cambridge, MA (US)

(72) Inventors: Aron H. Blaesi, Cambridge, MA (US); Nannaji Saka, Cambridge, MA (US)

(73) Assignee: Aron H. Blaesi, Cambridge, MA (US)

( * ) Notice: Subject to any disclaimer, the term of this patent is extended or adjusted under 35 U.S.C. 154(b) by 351 days.

(21) Appl. No.: 15/482,776

(22) Filed: Apr. 9, 2017

(65) Prior Publication Data

US 2018/0049993 A1    Feb. 22, 2018

Related U.S. Application Data

(60) Provisional application No. 62/377,068, filed on Aug. 19, 2016, provisional application No. 62/446,431, (Continued)

(51) Int. Cl.
| | |
|---|---|
| *A61K 9/70* | (2006.01) |
| *A61K 9/20* | (2006.01) |
| *B29C 64/106* | (2017.01) |
| *B33Y 10/00* | (2015.01) |
| *B33Y 30/00* | (2015.01) |

(Continued)

(52) U.S. Cl.
CPC .............. *A61K 9/70* (2013.01); *A61K 9/2031* (2013.01); *A61K 9/2072* (2013.01); *A61K 31/167* (2013.01); *A61K 31/192* (2013.01); *A61K 47/10* (2013.01); *A61K 47/34* (2013.01); *B29C 64/106* (2017.08); *B33Y 10/00* (2014.12); *B33Y 30/00* (2014.12); *B33Y 70/00* (2014.12); *B33Y 80/00* (2014.12)

(58) Field of Classification Search
CPC ....................................................... A61K 9/70
See application file for complete search history.

(56) References Cited

U.S. PATENT DOCUMENTS

| | | |
|---|---|---|
| 4,291,015 A | 9/1981 | Keith et al. |
| 6,416,740 B1 | 7/2002 | Yoo et al. |

(Continued)

FOREIGN PATENT DOCUMENTS

| | | | | |
|---|---|---|---|---|
| EP | 0047492 A2 * | 3/1982 | ............. | A61L 15/42 |
| WO | WO-03057197 A1 * | 7/2003 | ................ | A61J 3/10 |

OTHER PUBLICATIONS

Ko et al. (Introduction to Nanofiber Materials, Cambridge University Press, 2014, p. 154-156 (Year: 2014).*

*Primary Examiner* — Benjamin J Packard

(57) ABSTRACT

At present, the most prevalent pharmaceutical dosage forms, the oral immediate-release tablets and capsules, are granular solids. The problem of such solids is that their microstructure and properties are not predictable from physical models. As a consequence, product development and manufacture are resource-intensive and time-consuming, and quality control is statistical by testing instead of by design. Furthermore, the range of the drug release rate, and the variety of active ingredients that can be processed to a functional product, are limited in such dosage forms. Presented herein, accordingly, is a fibrous dosage form suitable for immediate-release applications prepared by a predictable liquid-based process. The fibrous dosage form includes a drug-containing solid comprising a three dimensional structural network of one or more drug-containing fibers.

38 Claims, 20 Drawing Sheets

Related U.S. Application Data filed on Jan. 14, 2017, provisional application No. 62/468,888, filed on Mar. 8, 2017.

(51) Int. Cl.
*B33Y 70/00* (2020.01)
*B33Y 80/00* (2015.01)
*A61K 31/167* (2006.01)
*A61K 31/192* (2006.01)
*A61K 47/10* (2017.01)
*A61K 47/34* (2017.01)

(56) References Cited

U.S. PATENT DOCUMENTS

| | | |
|---|---|---|
| 6,471,992 B1 | 10/2002 | Unger |
| 7,491,407 B2 * | 2/2009 | Pourdeyhimi ........... A61K 9/70 424/443 |
| 2003/0021845 A1 | 1/2003 | Friedman et al. |
| 2003/0035833 A1 | 2/2003 | He |
| 2003/0050711 A1 * | 3/2003 | Laurencin ................. A61F 2/28 623/23.72 |
| 2004/0028732 A1 | 2/2004 | Falkenhausen et al. |
| 2004/0166153 A1 | 10/2004 | McAllister et al. |
| 2005/0147670 A1 | 7/2005 | Hsu et al. |
| 2011/0105441 A1 | 5/2011 | Zhang et al. |
| 2014/0023708 A1 | 1/2014 | Harada et al. |
| 2014/0271530 A1 | 9/2014 | Tummala et al. |
| 2014/0356426 A1 | 12/2014 | Barnscheid et al. |
| 2015/0164816 A1 | 6/2015 | Jaklenec et al. |
| 2015/0246016 A1 | 9/2015 | Dyakonov et al. |
| 2016/0184230 A1 | 6/2016 | Blaesi et al. |
| 2017/0072105 A1 * | 3/2017 | Jeffries ................... A61L 27/54 |

\* cited by examiner

FIBROUS DOSAGE FORM

CROSS-REFERENCE TO RELATED APPLICATIONS

This application claims priority to and the benefit of, and incorporates herein by reference in their entirety, the U.S. Provisional Application Nos. U.S. 62/377,068 filed on Aug. 19, 2016, U.S. 62/446,431 filed on Jan. 14, 2017, and U.S. 62/468,888 filed on Mar. 8, 2017.

This application is related to, and incorporates herein by reference in its entirety, the U.S. application Ser. No. 14/907,891 filed on Jan. 27, 2016 and titled "Melt-Processed Polymeric Cellular Dosage Form". This application is also related to, and incorporates herein by reference in their entirety, the U.S. Provisional Application Nos. U.S. 62/360,546 filed on Jul. 7, 2016, and U.S. 62/446,808 filed on Jan. 16, 2017.

FIELD OF THE INVENTION

This invention relates generally to microstructures, compositions, and methods for drug release. In certain embodiments, the invention relates to fibrous dosage forms.

BACKGROUND OF THE INVENTION

The most prevalent pharmaceutical dosage forms 100 at present, the oral immediate-release tablets and capsules, are porous, granular solids 101 consisting of compressed drug 110 and excipient 120 particles as schematically shown in FIG. 1a. The excipient 120 and microstructure are designed to promote rapid disintegration of the dosage form 101 into its constituent particulates 110, 120 upon contact with gastrointestinal fluid. This promotes rapid dissolution of drug 110 in the gastrointestinal tract, and enables that a large fraction of the ingested drug is absorbed by the blood stream as detailed in the commonly owned references "Remington's Pharmaceutical Sciences XVIII", A. R. Gennaro (ed.), Mack Publishing, Easton, Pa., 1990; and M. E. Aulton, K. M. G. Taylor, "Aulton's pharmaceutics: The design and manufacture of medicines", fourth edition, Churchill Livingstone, London, U K, 2013.

Despite their ability to disintegrate rapidly upon contact with gastrointestinal fluid, and their widespread use and application, the microstructural details and manufacture of the granular dosage forms 101 are difficult to predict because processing granular matter is fraught with numerous difficulties. (Such difficulties are explained in detail in multiple commonly owned publications; see, e.g., H. M. Jaeger, S. R. Nagel, R. P. Behringer, "Granular solids, liquids, and gases", Rev. Mod. Phys. 68 (1996) 1259-1273; P. G. De Gennes, "Granular matter: a tentative view", Rev. Mod. Phys. 71 (1999) 374-382; F. J. Muzzio, T. Shinbrot, B. J. Glasser, "Powder technology in the pharmaceutical industry: the need to catch up fast", Powder Technol. 124 (2002) 1-7; and T. A. Bell, "Challenges in the scale-up of particulate processes—an industrial perspective", Powder Technol. 150 (2005) 60-71.)

Most importantly, during fabrication of the dosage form 101, mixing drug and excipient particles is hampered by particle segregation and agglomeration, and dispensing and compacting particulates is complicated by the uneven flow of granular matter. As a consequence, the design, development, and manufacture of granular forms must rely on statistical or empirical methods which are inferior to deterministic approaches in many ways.

Dosage forms prepared by a deterministic, predictable process could open opportunities to achieve faster product development, improved and more flexible product properties, and faster and more economical manufacture of products with reproducible quality. A predictable dosage form manufacturing process could be achieved by liquid-based processing, as the streamlines in laminar flow follow known pathways, with flow rates that can be calculated from "constitutive" models.

As the manufacturing process is changed from granular to liquid-based processing, however, the microstructural details of the resulting dosage forms 100 are changed, too. The solidification of a melt or the drying of a paste, for example, yields a non-porous (or minimally-porous), solid microstructure 102 as shown in FIG. 1b. The disintegration rate of such non-porous solids is limited by diffusion processes in either transporting dissolution fluid to the interior of the dosage form or the removal of material from the solid to the fluid. Because the specific surface area of non-porous forms 102 is small, the disintegration rate is much smaller than that of the granular structure 101. As a result, the non-porous structures 102 are not suited for immediate drug release if the dosage forms 102 are several millimeters thick. It is thus necessary to design dosage forms and predictable manufacturing processes that provide both a wide range in drug release properties and predictable and economical processing.

Therefore, in the U.S. patent application Ser. No. 14/907,891 and the publications in J. Control. Release, 220 (2015) 397-405; Eur. J. Pharm. Biopharm, 103 (2016) 210-218; Int. J. Pharm. 509 (2016) 444-453; and Chem. Eng. J. 320 (2017) 549-560, the present inventors (Blaesi and Saka) have introduced cellular dosage forms prepared from polymeric melts. The cellular structures are a solid skeleton 103 of drug 113 and excipient 123, and gas-filled voids or cells 130, 140 (FIG. 1c). The cells are closed 130 if the solid material is distributed in thin walls 150 that form the faces of the cells; they can be interconnected, or open 140, if certain walls are absent or removed and the solid material is distributed in the cell edges 160 only. In prior work, the cell structures 103 were prepared by the nucleation and growth of gas bubbles in a drug-laden polymer melt, and by mechanical insertion of the bubbles in a micro- or milli-fluidic melt channel. When the volume fraction of voids was small, the cells were mostly closed 130. But as the volume fraction of voids was increased to about 0.4-0.5 or greater, topologies with a fraction of the walls 150 removed and clusters of interconnected void space (also referred to here as "free space") 140 could be obtained.

The drug release rate is accelerated substantially as the connectivity of the void space 130, 140 is increased. If channels exist with two open ends, then the dissolution medium is given passage to rapidly percolate to the interior of the structure 103. It can subsequently diffuse into the thin walls 150 and soften them until fragments of the structure 103 exfoliate. Dosage form 103 disintegration rates that are up to an order of magnitude greater than those of the corresponding solid materials 102 have been reported due to this mechanism, demonstrating that such highly porous cellular dosage forms 103 are suitable for immediate-release applications.

To achieve cell structures 103 with a fraction of walls 150 removed and a dosage form 103 with interconnected free spaces 140, some fluidic wall-films 150 must rupture during the melt process. Such rupture, however, is difficult to control and the occurrence and kinetics are highly composition-dependent.

Predictable fabrication of open-cell structures, for any composition, could be achieved by fibrous dosage forms. The fibrous dosage forms may, for example, be formed by 3D-micro-patterning a fibrous stream on a surface or in a mold. In such processes, the diameter of and the distance between the fibers may be precisely controlled by mechanical means. Therefore, in this disclosure, new microstructures and compositions of fibrous dosage forms are presented. It is expected that such fibrous dosage enable predictable drug release rates, a greater range of the drug release rate, and faster and more economical development and manufacture of dosage forms at reproducible quality.

SUMMARY OF THE INVENTION

Thus, in a first aspect, the present invention provides a pharmaceutical dosage form comprising a drug-containing solid having an outer surface and an internal structure contiguous with and terminating at said outer surface; said internal structure comprising a three dimensional structural network of one or more fibers; said fibers comprising at least one active ingredient and at least one excipient; said fibers further comprising fiber segments separated and spaced from adjoining fiber segments by free spacings; and the free spacings defining one or more free spaces in said drug-containing solid.

In certain embodiments, the one or more fibers comprise an average thickness no greater than 2.5 mm.

In certain embodiments, the free spacing between the fiber segments is so that the percolation time of physiological/body fluid into one or more interconnected free spaces of the dosage form is no greater than 900 seconds under physiological conditions.

In certain embodiments, the effective free spacing between the fiber segments across the one or more free spaces on average is greater than 0.1 µm.

In certain embodiments, a contact width between two fibers or two fiber segments is no greater than 2.5 mm.

In certain embodiments, the position of at least one fiber or at least one fiber segment in the three dimensional structural network of one or more fibers is precisely controlled.

In certain embodiments, the volume fraction of fibers or fiber segments with precisely controlled position in the three dimensional structural network of one or more fibers is greater than 0.3.

In certain embodiments, the three dimensional structural network of one or more fibers comprises an ordered structure.

In certain embodiments, the inter-fiber spacing and fiber thickness are precisely controlled.

In certain embodiments, a volume fraction of the drug containing fibers with respect to a representative control volume of the dosage form is no greater than 0.98.

In certain embodiments, at least one excipient is wettable by a physiological/body fluid under physiological conditions.

In certain embodiments, at least one excipient is soluble in a physiological/body fluid and comprises a solubility greater than 0.1 g/l in said physiological/body fluid under physiological conditions.

In certain embodiments, dissolved molecules of the soluble excipient comprise a diffusivity greater than $1\times10^{-12}$ m$^2$/s in a physiological/body fluid under physiological conditions.

In certain embodiments, at least one excipient is absorptive of a physiological/body fluid, and wherein rate of penetration of the physiological/body fluid into a fiber or said absorptive excipient under physiological conditions is greater than the average fiber thickness divided by 3600 seconds.

In certain embodiments, at least one excipient is absorptive of a physiological/body fluid, and wherein an effective diffusivity of physiological/body fluid in a fiber or said absorptive excipient is greater than $0.5\times10^{-11}$ m$^2$/s under physiological conditions.

In certain embodiments, at least one excipient transitions from solid to a fluidic or gel consistency solution upon contact with a volume of physiological/body fluid equal to the volume of the one or more free spaces of the dosage form, said solution having a viscosity less than 500 Pa·s under physiological conditions.

In certain embodiments, at least one excipient is a polymer with molecular weight between 0.8 kg/mol and 2000 kg/mol.

In certain embodiments, at least one of the wettable excipients is selected from the group comprising polyethylene glycol (PEG), polyethylene oxide, polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, or butylmethacrylat-(2-dimethylaminoethyl)methacrylat-methylmathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, or hydroxypropyl methylcellulose), starch, polylactide-co-glycolide, polyvinyl caprolactam-polyvinyl acetate-polyethylene glycol graft copolymer, lactose, starch derivatives (e.g., pregelatinized starch or sodium starch glycolate), chitosan, pectin, acrylic acid crosslinked with allyl sucrose or allyl pentaerythritol (e.g., carbopol), and polyacrylic acid.

In certain embodiments, a free space is filled with a matter selected from the group comprising gas, liquid, or solid, or combinations thereof, and wherein said matter is partially or entirely removed upon contact with a physiological/body fluid under physiological conditions.

In certain embodiments, the gas comprises at least one of air, nitrogen, $CO_2$, argon, or oxygen.

In certain embodiments, the pharmaceutical dosage form has at least one dimension greater than 1 mm.

In certain embodiments, the disintegration time of said dosage form is less than 45 minutes.

In certain embodiments, the fibers form the edges of cells defining the free spaces.

In certain embodiments, the free spaces are interconnected.

In certain embodiments, plies of fibers or fiber segments are stacked in a cross-ply arrangement to form a three dimensional structure.

In certain embodiments, at least one fiber or at least one segment of a fiber is bonded to a second fiber or a second fiber segment to form an assembled structural element; said assembled structural element comprising one of: (a) a zero-dimensional structural element; (b) a one-dimensional structural element; (c) a two-dimensional structural element.

In certain embodiments, at least one fiber or at least one segment of a fiber is bonded to a second fiber or a second fiber segment to form a wall.

In certain embodiments, less than twelve walls must be ruptured to obtain an interconnected cluster of free space from the outer surface of the drug-containing solid to any point in the internal structure, where the average wall thickness is greater than 100 μm.

In certain embodiments, less than twenty four walls must be ruptured to obtain an interconnected cluster of free space from the outer surface of the drug-containing solid to any point in the internal structure, where the average wall thickness is smaller than 100 μm.

In certain embodiments, the dosage form has a coating covering its outer surface.

In certain embodiments, the greater of the dosage form's tensile strength or yield strength exceeds 0.005 MPa.

In certain embodiments, the dosage form further comprises another drug-containing solid, said solid comprising at least one active ingredient.

In certain embodiments, one or more excipients serve as fillers, stabilizers, preservatives, taste maskers, sweeteners, colorants, processing aids, or any other excipient functionality.

In a second aspect, the present invention provides a pharmaceutical dosage form comprising a drug-containing solid having an outer surface and an internal structure contiguous with and terminating at said outer surface; said internal structure comprising a three dimensional structural network of one or more fibers; said fibers comprising at least one active ingredient and at least one excipient; said fibers further comprising fiber segments separated and spaced from adjoining fiber segments by free spacings; and the free spacings defining one or more free spaces in said drug-containing solid; wherein the one or more fibers comprise an average thickness between 2 μm and 2.5 mm; the effective free spacing between the fiber segments across the one or more free spaces on average is greater than 0.1 μm; at least one dimension of the dosage form is greater than 1 mm; and at least one excipient comprises a solubility greater than 0.1 g/l in a physiological/body fluid under physiological conditions or at least one excipient is absorptive of a physiological/body fluid, and wherein rate of penetration of the physiological/body fluid into a fiber or an absorptive excipient under physiological conditions is greater than average fiber thickness divided by 3600 seconds.

In a third aspect, the present invention provides a pharmaceutical dosage form comprising a drug-containing solid having an outer surface and an internal structure contiguous with and terminating at said outer surface; said internal structure comprising a three dimensional structural network of one or more fibers; said fibers comprising at least one active ingredient; said fibers further comprising fiber segments separated and spaced from adjoining fiber segments by free spacings; and the free spacings defining one or more free spaces in said drug-containing solid; wherein the one or more fibers comprise an average thickness no greater than 2.5 mm; and the effective free spacing between the fiber segments across the one or more free spaces on average is greater than 0.1 μm; and at least one dimension of the dosage form is greater than 1 mm.

In certain embodiments, the one or more fibers comprise an average thickness greater than 1.75 μm.

In certain embodiments, at least one fiber or at least one segment of a fiber is bonded to a second fiber or a second fiber segment to form an assembled structural element; said assembled structural element comprising one of: (a) a zero-dimensional structural element; (b) a one-dimensional structural element; (c) a two-dimensional structural element.

Elements of embodiments described with respect to one aspect of the invention can be applied with respect to another aspect. By way of example but not by way of limitation, certain embodiments of the claims described with respect to the first aspect can include features of the claims described with respect to the second or third aspect, and vice versa.

This invention may be better understood by reference to the accompanying drawings, attention being called to the fact that the drawings are primarily for illustration, and should not be regarded as limiting. The scope of the invention is limited only by the claims and not by the drawings or description herein.

BRIEF DESCRIPTION OF THE DRAWINGS

The objects, embodiments, features, and advantages of the present invention are more fully understood when considered in conjunction with the following accompanying drawings.

DEFINITIONS

Figure 1:
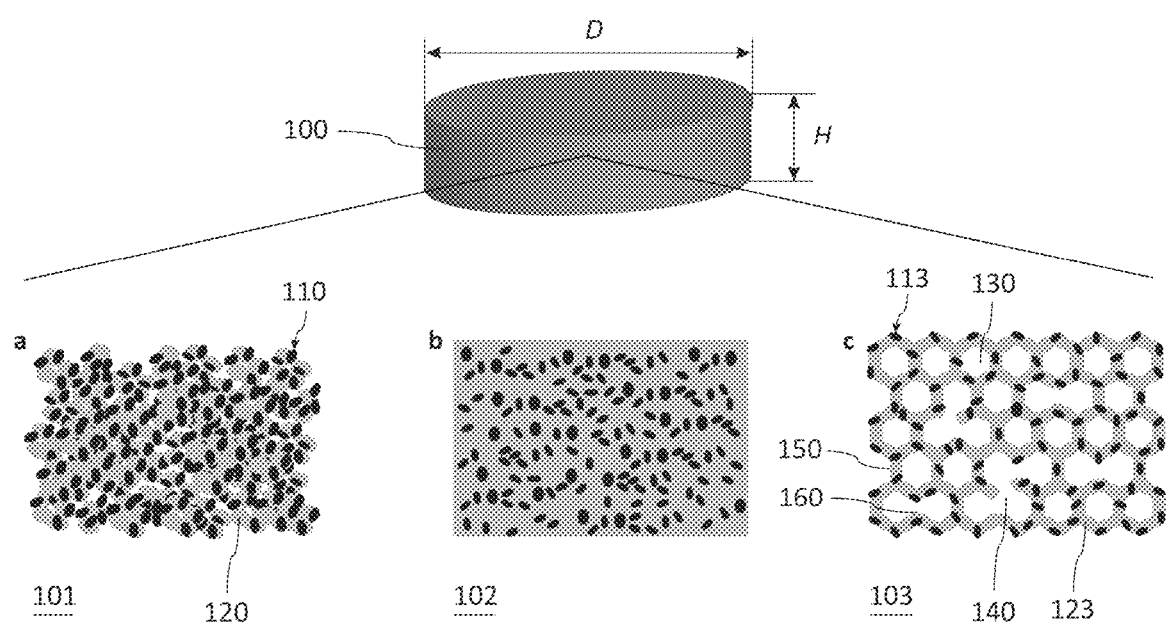
FIG. 1 shows schematics of microstructures of (a) prior art granular dosage forms, (b) melt-processed non-porous dosage forms, and (c) melt-processed cellular dosage forms.

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Moreover, in the disclosure herein, the terms "one or more active ingredients" and "drug" are used interchangeably. As used herein, an "active ingredient" or "active agent" refers to an agent whose presence or level correlates with elevated level or activity of a target, as compared with that observed absent the agent (or with the agent at a different level). In some embodiments, an active ingredient is one whose presence or level correlates with a target level or activity that is comparable to or greater than a particular reference level or activity (e.g., that observed under appropriate reference conditions, such as presence of a known active agent, e.g., a positive control).

In the context of the invention herein, a three dimensional structural network of drug-containing fibers (also referred to herein as "three dimensional fiber network structure") generally comprises a drug-containing fibrous structure (e.g. an assembly or an assemblage or an arrangement of one or more drug-containing fibers) that extends over a length, width, and thickness greater than the thickness of a fiber. Furthermore, in some contexts of the invention herein, a three dimensional structural network of drug-containing fibers may comprise a drug-containing fibrous structure (e.g., an assembly or an assemblage or an arrangement of one or more drug-containing fibers) that extends over a length, width, and thickness greater than 300 μm. This includes, but is not limited to drug-containing fibrous structures that extend over a length, width, and thickness greater than 500 μm, or greater than 700 μm, or greater than 1 mm, or greater than 1.25 mm, or greater than 1.5 mm, or greater than 2 mm.

As used herein, the terms "fiber", "fibers", "one or more fibers", "one or more drug-containing fibers", and "drug-containing fibers", are used interchangeably. They are understood as the solid, drug-containing structural elements (or building blocks) that make up the three dimensional structural network (e.g., the dosage form structure). A fiber has a length much greater than its width and thickness. In the present disclosure, a fiber is referred to as having a length greater than 2 times its width and thickness (e.g., the length is greater than 2 times the fiber width and the length is greater than 2 times the fiber thickness). This includes, but is not limited to a fiber length greater than 3 times, or greater than 4 times, or greater than 5 times, or greater than 6 times, or greater than 8 times, or greater than 10 times, or greater than 12 times the fiber width and thickness. In other embodiments that are included but not limiting in the disclosure herein, the length of a fiber may be greater than 0.3 mm, or greater than 0.5 mm, or greater than 1 mm, or greater than 2.5 mm.

Moreover, as used herein, the term "fiber segment" refers to a fraction of a fiber along the length of said fiber.

In the invention disclosed herein, fibers (or fiber segments) may be bonded, and thus they may serve as building blocks of "assembled structural elements" with a geometry different from that of the original fibers. Such assembled structural elements include two-dimensional elements (or 2-dimensional structural elements), one-dimensional elements (or 1-dimensional structural elements), or zero-dimensional elements (or 0-dimensional structural elements).

As used herein, a two-dimensional structural element is referred to as having a length and width much greater than its thickness. In the present disclosure, the length and width of a two-dimensional structural element are greater than 2 times its thickness. An example of such an element is a "sheet". A one-dimensional structural element is referred to as having a length much greater than its width or thickness. In the present disclosure, the length of a one-dimensional structural element is greater than 2 times its width and thickness. An example of such an element is a "fiber". A zero-dimensional structural element is referred to as having a length and width of the order of its thickness. In the present disclosure, the length and width of a zero-dimensional structural element are no greater than 2 times its thickness. Furthermore, the thickness of a zero-dimensional element is less than 2.5 mm. Examples of such zero-dimensional elements are "particles" or "beads" and include polyhedra, spheroids, ellipsoids, or clusters thereof.

In the context of the invention disclosed herein, drug release from a solid fiber (or a solid dosage form, or a solid matrix, or a drug-containing solid) refers to the conversion of drug (e.g., one or more drug particles, or drug molecules, or clusters thereof, etc.) that is/are embedded in or attached to the solid fiber (or the solid dosage form, or the solid matrix, or the drug-containing solid) to drug in a dissolution medium. If the drug is embedded in a polymeric excipient or matrix, the drug may be released from said polymeric matrix as soon as said polymeric matrix has converted to a dilute solution (e.g., a liquid in which the excipient concentration is smaller than its solubility or "interfacial concentration").

Similarly, in the invention disclosed herein, a polymeric excipient matrix may be considered disintegrated if said polymeric matrix has converted to a gel with polymer concentration smaller than the "interfacial concentration" (e.g., as soon as the polymer has converted to a dilute solution).

In this application, the term "interfacial concentration" is referred to as the polymer concentration which separates the "solid" and "liquid" regions of a polymer eroding into a dissolution medium. It is typically of the order of the disentanglement concentration, $c_p$, of said polymer in a dissolution medium (or of the order of the solubility of said polymer in a dissolution medium).

Finally, as used herein, the terms "dissolution medium", "physiological/body fluid", "dissolution fluid", "medium", "fluid", and "penetrant" are used interchangeably. They are understood as any fluid produced by or contained in a human body under physiological conditions, or any fluid that resembles a fluid produced by or contained in a human body under physiological conditions. Examples include, but are not limited to: water, saliva, stomach fluid, gastrointestinal fluid, saline, etc. at a temperature of 37° C. and a pH value adjusted to the specific physiological condition.

DETAILED DESCRIPTION OF THE INVENTION

Dosage Form Structures

Figure 2:
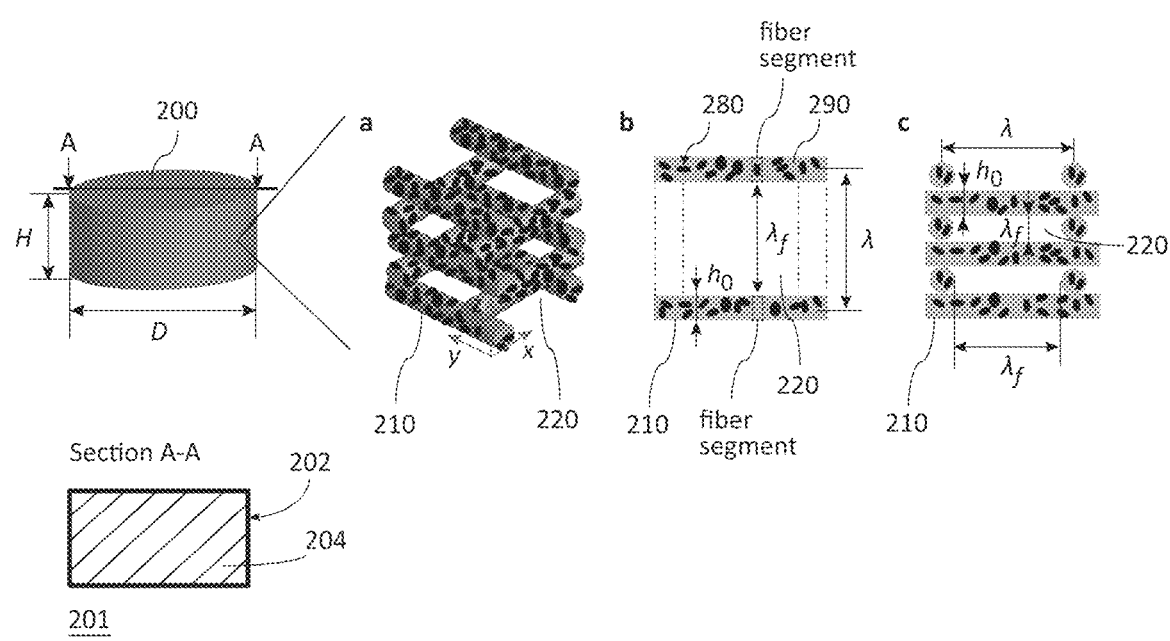
FIG. 2 is an example microstructural topology of a fibrous dosage form according to this invention.
Figure 3:
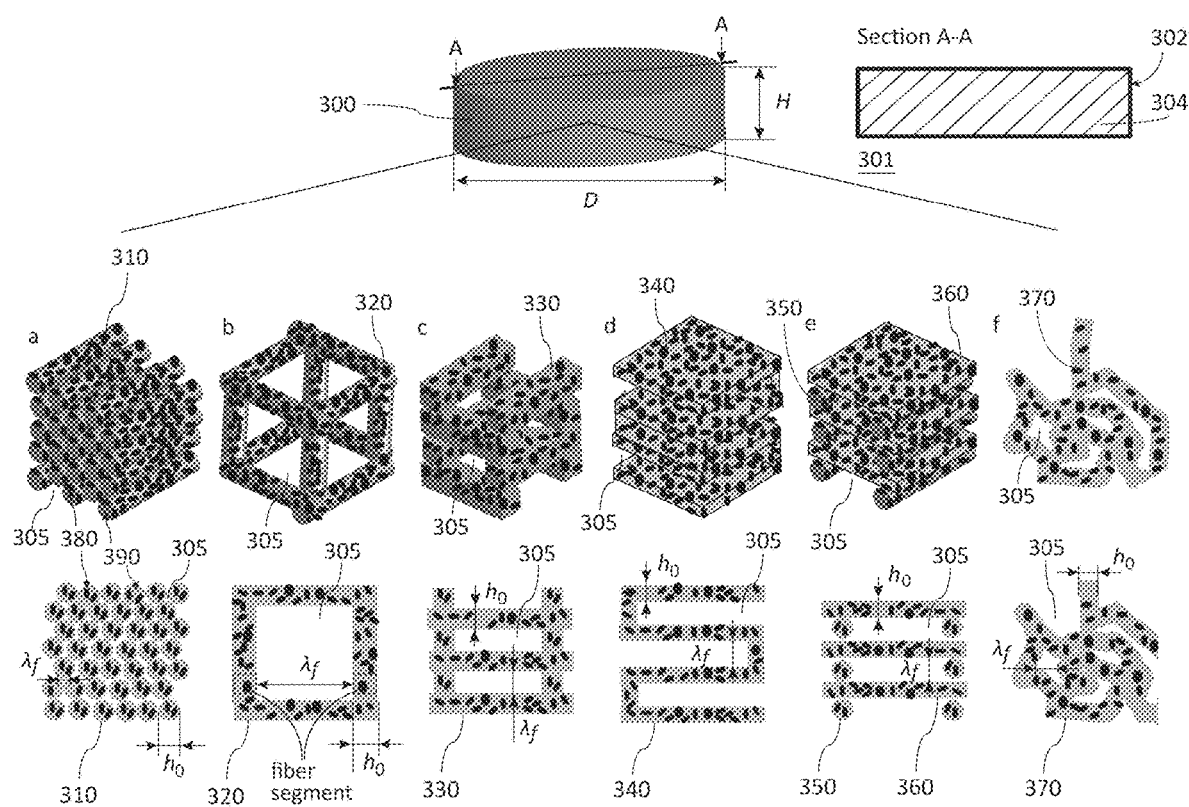
FIG. 3 depicts schematic diagrams of the microstructure of additional embodiments of solid dosage forms according to this invention.

FIGS. 2 and 3 present non-limiting examples of pharmaceutical dosage forms 200, 300 comprising a drug-containing solid 201, 301 having an outer surface 202, 302 and an internal structure 204, 304 contiguous with and terminating at said outer surface 202, 302. The internal structure 204, 304 comprises a three dimensional structural network of one or more drug-containing fibers 210, 310, 320, 330, 340, 350, 360, 370 (e.g., a three dimensional fiber network structure). The fibers further comprise fiber segments separated and spaced from adjoining fiber segments by free spacings, $\lambda_f$, which define one or more free spaces 220, 305 in the drug-containing solid 201, 301. The fibers 210, 310, 320, 330, 340, 350, 360, 370 may be oriented (e.g., arranged or structured) in a variety of ways, ranging from random (e.g., disordered) to partially regular (e.g., partially ordered) to regular (e.g., ordered or not random).

FIG. 2 shows a dosage form 200 with cross-ply arrangement (or structure) of fibers 210 with circular cross section (e.g., plies of fibers 210, or fiber segments, are stacked together in a cross-ply arrangement to form a three dimensional structure or structural network). The fibers in a plane (or ply or layer) are oriented in one direction but the fibers in the planes (or plies or layers) above and below are oriented transversely, or at an angle. This arrangement (or structure, or three dimensional structural network) is ordered and provides control of two structural variables essential for tailoring the properties of the dosage form: the fiber diameter, $D_f = 2R$, (or the average fiber thickness, $h_0$) and the inter-fiber spacing, $\lambda$, in a plane (or alternatively the free spacing, $\lambda_f$). The free spaces 220 around the fibers 210 are intrinsically connected in this arrangement, and together with the fibers form unit cells of volume $4R\lambda^2$. Thus by the commonly used terminology to describe cellular structures (see, e.g., M. F. Ashby, "The mechanical properties of cellular solids", Metall. Trans. A, 14A (1983) 1755-1769; L. J. Gibson, M. F. Ashby, "Cellular solids: structure and properties", second edition, Cambridge University Press, 1999; and the examples of FIG. 1 and FIG. 12 of the specification herein), the fibers 210 simply form the edges of open cells defining the free spaces 220 and there are no walls or faces.

Several relevant structural parameters can be derived for this configuration. For example, the volume fraction of the drug-containing fibers, $\varphi_f$, with respect to the volume of the dosage form 200 (or the volume of the drug-containing solid 201 or a representative control volume of the dosage form) is:

$$\phi_f = \frac{\pi}{2}\frac{R}{\lambda} \tag{1a}$$

The specific surface area (area per unit volume of fibers 210), $A_s$, is given by:

$$A_s = \frac{2}{R} \tag{1b}$$

The length of fibers 210 per unit volume of the dosage form, $l_v$, is:

$$l_v = \frac{\phi_f}{\pi R^2} = \frac{1}{2R\lambda} \tag{1c}$$

Also, the surface area of fibers 210 per unit volume of the dosage form 200 (or a representative control volume), $A_v$, is:

$$A_v = \frac{2\phi_f}{R} = \frac{\pi}{\lambda} \tag{1d}$$

It will become obvious to a person of ordinary skill in the art after reading this specification carefully that $\varphi_f$, $A_s$, $l_v$, and $A_v$, affect the disintegration rate and other relevant properties of a fibrous dosage form. Furthermore, it would be obvious to a person of ordinary skill in the art that Eqs. (1a)-(1d) must be adapted if the structure/arrangement/assembly (e.g. the three dimensional structural network) of fibers is changed.

Other non-limiting three dimensional structural networks of fibers are presented in FIG. 3. FIG. 3a shows a dosage form 300 with unidirectionally aligned drug-containing fibers 310 that are (almost) closely packed. FIG. 3b is an example of a structure with interpenetrating fibers 320 and FIG. 3c shows a cross-ply arrangement of fibers with square cross section 330. FIG. 3d is a non-limiting example of a structure consisting of fibers that are bonded to each other to form a continuous 2-dimensional structural element (for example, a sheet) 340. One such 2-dimensional structural element may, for example, be so configured that it forms the drug-containing solid (or the dosage form). Alternatively, several 2-dimensional elements may be stacked to form the drug-containing solid (or the dosage form). FIG. 3e presents a structure comprising a combination of fibers 350 and sheets 360. FIG. 3f shows an example of a structure with random or almost random arrangement/assembly of one or more fibers 370 (e.g. a structure that is disordered).

Figure 4:
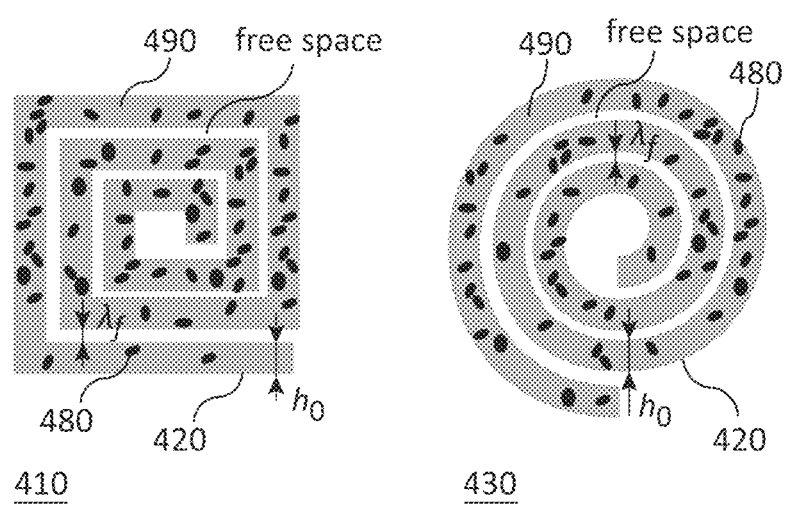
FIG. 4 presents schematic diagrams of microstructures of yet additional embodiments of solid dosage forms according to this invention.

Yet other non-limiting examples of three dimensional structural networks of fibers are shown in FIG. 4, which presents a top view of fibers 420 in a plane forming a rectangular structure 410, as well as a top view of fibers 420 in a plane forming a circular (or elliptical) structure 430.

More examples of how the fibers may be structured, arranged, or assembled would be obvious to a person of ordinary skill in the art. All of them are within the spirit and scope of this invention.

Compositions and Material Structures of Fibers

The fibers typically consist of one or more active ingredients 280, 380, 480 (also referred to here as "drug"), and in most cases also one or more excipients 290, 390, 490 (also referred to here as "excipient"). If a fiber consists of at least one active ingredient and at least one excipient, the drug and excipient may be structured in the fiber in an ordered or "partially or completely disordered" manner. Moreover, by way of example but not by way of limitation, the structural features of the drug or the excipient in the fibers may, for example, comprise particles, beads, polygons, ellipsoids, cubes, tubes, rods, etc., or combinations thereof, and have a size at the nano-, micro-, meso-, or macro-scale.

More such examples of compositions and material structures of fibers would be obvious to a person of ordinary skill in the art. All of them are within the scope of this invention.

Drug Release from Fibers

If the composition of a fiber consists of drug only, or if the drug is interconnected in the material structure of the fiber, the drug may be in direct contact with dissolution fluid upon immersion of the fiber in a medium. Thus, in some embodiments, the drug may be released from the fiber by dissolution of drug into the medium.

Figure 5:
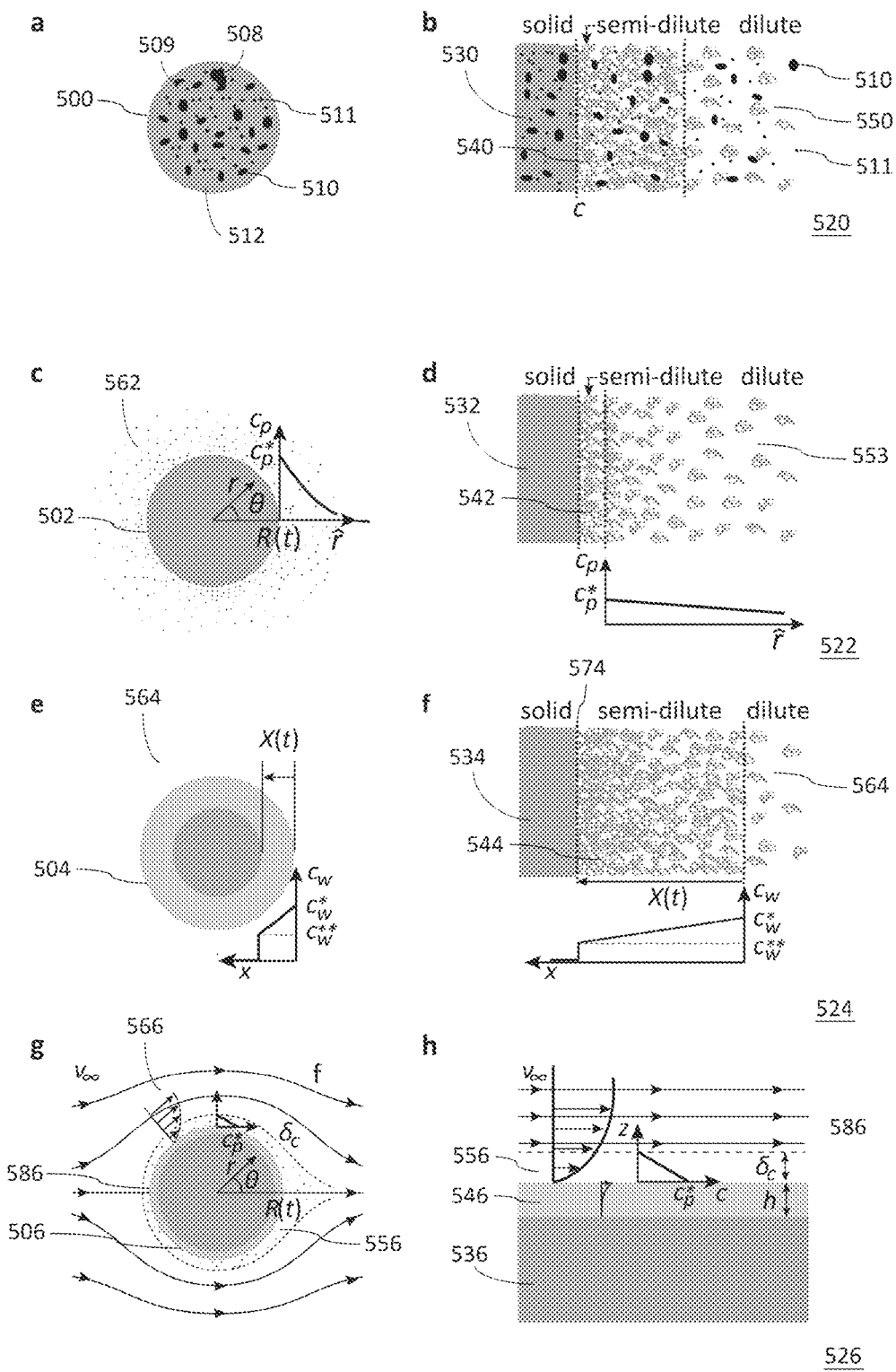
FIG. 5 schematically shows microstructure and disintegration of a single fiber by interdiffusion of polymeric excipient molecules and dissolution fluid in both stagnant (not stirred) and stirred media.

If the material structure of a fiber 500, however, comprises one or more discontinuous clusters of at least one drug particle 508, 510 or at least one drug molecule 509, 511 surrounded by a solid excipient 512 as shown in FIG. 5a, erosion or swelling of the excipient 512 is a prerequisite for drug release from the fiber 500. Two non-limiting examples of how drug may be released from such fibers 500 are presented below.

In the first non-limiting example, the excipient comprises an erodible polymer. Thus, as soon as the fiber 500 is brought in contact with dissolution medium, the medium diffuses into the excipient. The penetrant molecules (e.g., the dissolution fluid that diffused into the solid excipient) may then induce the solid excipient to swell (e.g., to increase in volume) and to transition from a solid to a fluidic or gel consistency solution. Subsequently, the polymer molecules from the gel consistency solution may diffuse or erode into the dissolution medium. The drug may be released from the fiber 500 as soon as the excipient has converted to dissolved molecules or a gel with polymer concentration smaller than the "interfacial concentration".

The "interfacial concentration" is referred to in this application as the polymer concentration which separates the "solid" and "liquid" regions. For a typical polymer that erodes into a dissolution fluid, the interface is diffuse, and thus the interfacial concentration is difficult to determine precisely. As schematically shown in FIG. 513, the diffuse interface may extend over a layer 540 of non-negligible but finite thickness. It may be considered a semi-dilute gel consistency solution between the entangled, concentrated, and viscous polymer 530 (i.e., the "solid" or "semi-solid") and the dilute, low-viscosity dissolution medium 550 (i.e., the "liquid"). Thus, typically, the concentration of an eroding polymer in the semi-dilute interfacial layer 540 (e.g., the "interfacial concentration") is between the disentanglement concentration, $c_p^*$, of said polymer in a dissolution medium, and about the concentration, $c_p^{**}$, at which a solution comprising said polymer and a dissolution fluid becomes concentrated. (For further information, see e.g., P. G. De Gennes, "Scaling concepts in polymer physics", fifth ed., Cornell University Press, 1996; or M. Doi, S. F. Edwards, "The theory of polymer dynamics", Oxford University Press, 1986).

In the second non-limiting example, the excipient comprises an absorptive or swellable polymer. Thus upon immersion of the fiber in a dissolution fluid, the fluid diffuses into the solid polymeric excipient. The penetrant molecules (e.g., the dissolution fluid that diffused into the solid excipient) may then convert part or all of the solid drug enclosed in the polymeric excipient to dissolved drug molecules. The mobility of drug molecules may be greater in the penetrated polymeric excipient than in the excipient without penetrant. Thus the drug molecules embedded in the penetrated excipient may diffuse to the dissolution medium swiftly, and drug may be released within the specific time requirements.

More examples of drug release from fibers would be obvious to a person of ordinary skill in the art. All of them are within the scope of this invention.

Modeling Fiber and Dosage Form Disintegration

The following examples set forth, in detail, ways by which the drug release and disintegration behavior of fibers and fibrous dosage forms may be modeled. The models will enable one of skill in the art to more readily understand the properties and advantages of the fibrous dosage forms. The models and examples are presented by way of illustration, and are not meant to be limiting in any way.

a) Fiber Erosion by Diffusion without Convection

FIGS. 5c and 5d show a non-limiting example of a circular polymeric fiber 502 and its interface 522 after immersion in an unstirred, infinite dissolution medium 562. The polymer molecules are assumed to diffuse away from the interface faster than the dissolution medium diffuses into the fiber. Thus after a short wait after immersion, the thickness of the diffuse, semi-dilute layer 542 is (and remains) thin compared with the fiber radius or the thickness of the dilute region 552. The dissolution rate (or the disintegration rate) of the fiber 502 may thus be described by the diffusion of polymer molecules from the fiber interface into the dilute medium. The initial rate of erosion of the fiber 502 may be approximated by:

$$\frac{dR}{dt} = -\frac{j_p}{\rho_e} \approx -\frac{c_p^*}{\rho_e}\sqrt{\frac{D_p}{\pi t}} \quad (2)$$

Integrating gives $$R(t) = R_0 - \frac{c_p^*}{\rho_e}\sqrt{\frac{4 D_p t}{\pi}} \quad (3)$$

where R(t) is the fiber radius as a function of time, $R_0$ is the initial fiber radius, $j_p$ the flux of the eroding polymer, $\rho_e$ the density of the solid polymer, $c_p^*$ the disentanglement concentration of the polymer (which is an estimate of the interfacial concentration and further described in Eq. (18) and FIGS. 24, 25, and 26 later), and $D_p$ the diffusivity of a polymer molecule in the dissolution medium.

By way of example but not by way of limitation, if $R_0=250$ μm, $c_p^*=163$ kg/m$^3$, $\rho_e=1150$ kg/m$^3$, $D_p=1.09\times10^{-10}$ m$^2$/s, the fiber radius decreases to about 210 μm after the time $t=R_0^2/D_p=9.5$ mins. Thus about 29% of the fiber are dissolved or disintegrated at this time in this example. By contrast, if the fiber radius is increased to 2.5 mm (a typical radius of a dosage form) and the other parameters are kept the same, only about 3% would be eroded 9.5 minutes after immersion in a still fluid. This percentage is an order of magnitude smaller than the corresponding value of a thin fiber, which exemplifies the advantage of a "thin" fiber over a "thick" fiber or dosage form for achieving fast disintegration (and high drug release) rates.

It would be obvious to a person of ordinary skill in the art that the model presented (and any of the following models) are readily adapted to fibers of non-circular cross sections. Such fibers include, but are not limited to fibers with square, rectangular, elliptical, polygonal, or any other cross section. Furthermore, more examples of models of erosion of a single fiber in a still dissolution medium would be obvious to a person of ordinary skill in the art. All of them are within the scope of this invention.

b) Diffusion of Dissolution Fluid into a Fiber

FIGS. 5e and 5f present another non-limiting example of a circular polymeric fiber 504 and its interfacial region 524 after immersion in a dissolution fluid 564 that is of infinite extent and stagnant (not stirred). Now it is assumed that water (or dissolution fluid) diffusion into the polymer is faster than polymer diffusion into the fluid. This is opposite of the previous case. In this model, the thickness of the gel-layer 544 grows with time as dissolution fluid continues to diffuse in. Under Fickian diffusion (see, e.g., J. Crank, "The Mathematics of Diffusion", second edition, Oxford University Press, 1975), the position of the solid/semi-dilute interface 574 is as follows, neglecting any form of erosion of the gelated layer:

$$X = k_d t^{1/2} \tag{4}$$

where t is time and $k_d$ a constant.

If a substantial amount of dissolution fluid diffuses into the fiber 504, it swells and the polymer density (or the polymer concentration) in the fiber is reduced. The radius of the swollen, gelated fiber, $R_{gel}$, may be estimated as $$R_{gel} = R_0 \left(\frac{\rho_e}{c_{gel}}\right)^{\frac{1}{n}} \tag{5}$$

where $R_0$ is the initial fiber radius, the exponent n=3 for a fiber that expands uniformly in 3 dimensions (n=2 for a fiber that expands radially only), $\rho_e$ is the density of the polymer in the solid/dry state, and $c_{gel}$ an average concentration of swellable polymer in the gel 544.

The entire fiber 504 is converted into a gel when $X=R_{gel}$. Thus by Eq. (4), the time taken by the dissolution fluid 564 to penetrate the fiber 504 (i.e., to convert it into a gel) may be estimated as:

$$t_{pen} = \frac{R_{gel}^2}{k_d} = \frac{R_0^2}{D_{eff}} \tag{6}$$

where $D_{eff}$ is an effective diffusivity of physiological/body fluid in the polymeric fiber under physiological conditions. By way of example but not by way of limitation, if $R_0=250$ μm and $D_{eff}=4\times10^{-10}$ m$^2$/s, by Eq. (6) $t_{pen}=156$ seconds. Conversely, if $R_0$ is increased to 2.5 mm and $D_{eff}$ remains unchanged, $t_{pen}$ increases to 260 minutes. Thus the penetration time of a "thin" fiber is much shorter than that of a "thick" fiber or a "thick" dosage form of the same composition.

It may be noted that the above equations can be readily adapted to multi-component fibers. Also, more such examples of models of diffusion of dissolution fluid into a single fiber would be obvious to a person of ordinary skill in the art. All of them are within the scope of this invention.

c) Disintegration of Penetrated Fibers

The penetrated fiber may be considered a polymeric solution (or dispersion or gel) that has a viscosity greater than the viscosity of the dissolution fluid. If the viscosity of the solution (e.g., the penetrated fiber, or even the penetrated fiber surface) is small enough, and if such external forces applied on the fiber as gravity, shear, or imbalances in fluid pressure are large enough, the penetrated fiber may be deformed or broken up into pieces. The pieces may then dissolve or disentangle rapidly in the dissolution fluid. Thus a fiber may be disintegrated soon after it is penetrated in such non-limiting situations.

In other cases without limitation, a swollen, gelated (or penetrated) fiber may, for example, erode by diffusion of polymer molecules into a stagnant dissolution medium. This situation is similar to the non-limiting example shown in FIG. 5c and FIG. 5d. If the radius of the swollen, penetrated fiber is greater than the radius of the corresponding dry fiber, the swollen fiber has a greater surface area and a smaller polymer concentration (or density) than the dry fiber. Thus the swollen fiber disintegrates faster than the dry fiber in these non-limiting cases.

In both cases introduced above, the diffusion of dissolution fluid into the fiber contributes to faster fiber disintegration. "Thin" fibers are penetrated faster than "thick" fibers or "thick" minimally-porous dosage forms. "Thin" fibers are therefore preferred to meet immediate-release specifications, the most relevant requirement of a typical pharmaceutical dosage form.

d) Fiber Erosion with Convection

In a stirred medium, the moving dissolution fluid 566 may impose a shear stress on the fiber surface 586 (i.e., the surface of the gelated layer) and a concentration boundary layer 556 may develop around a fiber 506 as schematically shown in FIGS. 5g and 5h. Within the boundary layer, the concentration gradient is substantial, but outside the layer it is negligible. The concentration boundary layer thickness, $\delta_c$, may decrease with increasing fluid velocity, or the Reynolds number. Hence the concentration gradient in the dissolution fluid 566 and thus also the material removal rate by convection of the eroding molecules away from the fiber surface 586 may increase.

In cross flow with Reynolds number, $Re=2Rv_\infty \rho_f/\mu_f \sim 1$ or smaller, the time to erode 80% of the content of a circular fiber of initial radius, $R_0$, may be estimated as:

$$t_E \cong 0.71 \times \frac{\rho_e}{c_p^*} \frac{R_0^{5/3}}{D_p^{2/3} v_\infty^{1/3}} \tag{7}$$

where $v_\infty$ is the far-field velocity of the dissolution medium, $\rho_e$ the density of the eroding polymer in the fiber, $c_p^*$ an estimate of the interfacial concentration, and $D_p$ the diffusivity of a polymer molecule in the dissolution medium.

By way of example but not by way of limitation, if $R_0=250$ μm, $c_p^*=163$ kg/m$^3$, $\rho_e=1150$ kg/m$^3$, $D_p=1.09\times10^{-10}$ m$^2$/s, and $v_\infty=10$ mm/s, by Eq. (7) $t_E=1.7$ mins. By contrast, if a fiber with initial radius $R_0=2.5$ mm would erode under the same conditions, the erosion time, $t_E=77.8$ min. Thus also in this non-limiting example, the "thin" fiber disintegrates at least an order of magnitude faster than the "thick" fiber or the "thick" minimally-porous dosage form.

Any more examples of models of fiber erosion with convection would be obvious to a person of ordinary skill in the art. All of them are within the scope of this invention.

e) Dosage Form Disintegration in a Stagnant Medium

Figure 6:
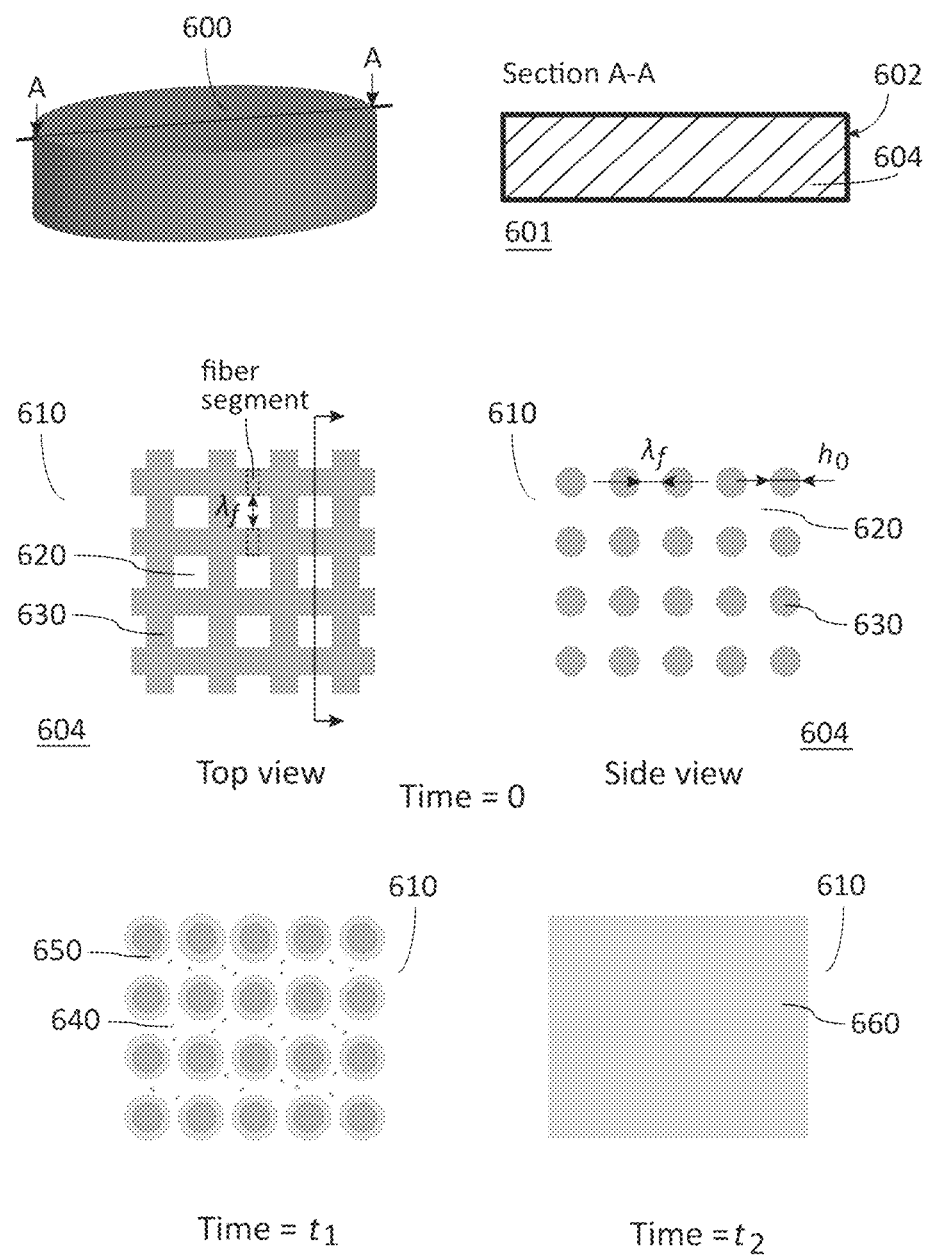
FIG. 6 schematically presents the time-dependent conversion of a fibrous structure into a polymer-dissolution fluid solution after immersion of the fibrous structure in a stagnant dissolution fluid.

FIG. 6 presents a non-limiting example of the disintegration process of a fibrous dosage form 600 in a stagnant dissolution fluid 610. The fibrous dosage form 600 comprises a drug-containing solid 601 having an outer surface 602 and an internal structure 604 contiguous with and terminating at said outer surface 602. The internal structure 604 comprises a three dimensional structural network of fibers 630. The fibers 630 contain an active ingredient and a polymeric excipient that is absorptive of or soluble in (e.g., erodible by) a dissolution medium 610. The fibers 630 further comprise fiber segments separated and spaced from adjoining segments by free spacings, $\lambda_f$, which define one or more free spaces 620 in the drug-containing solid 601.

Upon immersion of the dosage form 600 in a dissolution fluid 610, the free spaces 620 may be percolated rapidly by the fluid 610 if (a) the free spaces 620 are (partially or entirely) inter-connected, (b) the content of the free spaces 620 is partially or entirely removable by the dissolution fluid 610, (c) the free spacing, $\lambda_f$, (e.g., the "free" distance between the one or more fibers) is on the sub-micro-, micro-, or meso-scale or greater, and (d) the excipient in the fiber is wettable by the dissolution fluid if $\lambda_f$ is on the sub-micro-, or micro-scale. Thus if the above conditions are satisfied, a fiber 630 in the three dimensional structural network will be surrounded by the dissolution fluid 610 soon (e.g. in less than about a second) after immersion of the dosage form 600. It is assumed that this is the case in the non-limiting example described here. The time to percolate part or all of the free spaces 620 is thus not considered to be rate-determining in dosage form disintegration or drug release.

Subsequent to fluid 610 percolation to the interior of the drug-containing solid 604, the dissolution fluid 610 that surrounds a fiber segment then penetrates into it by diffusion, and the segment may swell and erode. Upon inter-diffusion of the fluid 610 and the polymeric fiber segment, polymer molecules 640 (and gel-layer 650) may spread out. They may intersect with the molecules of adjoining fiber segments at a certain time, $t_1$, after immersion. Then at $t_2$ a polymer-fluid solution 660 is formed. The time $t_2$ to convert the drug-containing solid 604 to such a solution 660 may be estimated by the penetration and erosion times of a single fiber (or a single fiber segment) 630 in a stagnant fluid 610 (e.g. by Eqs. (3) and (6)).

If all the free spaces 620 are percolated by the dissolution fluid 610, and the drug containing solid 601 further does not expand as it is converted to a solution 660, the concentration of the excipient polymer, $c_{p,sol}$, in the solution 660 is about:

$$c_{p,sol} = \frac{M_e}{V_e + V_{fs}} = \frac{\phi_f \phi_e \rho_e}{1 - \phi_f(1-\phi_e)} \quad (8)$$

where $M_e$ is the mass and $V_e$ the volume of the absorptive/soluble excipient, $V_{fs}$ the volume of the free spaces 620, $\phi_f$ the volume fraction of the solid/dry fibers in the dry dosage form, $\phi_e$ the volume fraction of the absorptive/soluble excipient polymer in the dry fibers 630, and $\rho_e$ is the density of the excipient in the dry state.

The solution 660 is dilute and the polymer molecules disentangled if the polymer concentration in the solution 660, $c_{p,sol} \leq c_p^*$. This is the case if:

$$\phi_f \leq \frac{c_p^*}{(1-\phi_e)c_p^* + \phi_e\rho_e} \quad (9)$$

Thus if Eq. (9) is satisfied, the polymer concentration in, or the viscosity of, the solution 660 is so small that the solution 660 is dilute or almost dilute. Consequently, the fibrous dosage form can be considered disintegrated as soon the single fibers (or fiber segments) 630 are eroded or penetrated. Dosage form 600 disintegration is determined solely by the behavior of a single fiber 630, and the inter-fiber interactions may be neglected. Thus for a fiber 630 geometry and properties of the composition as in the non-limiting examples a and b above, the dosage form 600 is disintegrated just a few minutes after immersion. This is well within immediate-release specification, which is one of the most relevant requirements of a typical pharmaceutical dosage form 600.

If the concentration of polymer in the solution 660, $c_{p,sol} \gg c_p^*$, however, the solution 660 may be considered a viscous mass. The viscous mass (or the viscous solution, or the viscous dosage form) then erodes from its exterior surface by diffusion. The diffusion flux of the eroding polymer, $j_p$, may be written as:

$$j_p = \frac{c_p^* \sqrt{D_p}}{\sqrt{\pi t}} \quad (10)$$

and the time to disintegrate a thickness, $H_{dis}$, of the viscous mass 660 eroding from both faces is $$t_{dis} = \frac{H_{dis}}{2} c_{p,sol} \left(\frac{1}{t_{dis}} \int_0^{t_{dis}} j_p dt\right)^{-1} = \frac{\pi}{8}\left(\frac{c_{p,sol}}{c_p^*}\right)^2 \frac{H_{dis}^2}{D_p} \quad (11)$$

Thus by way of example but not by way of limitation, if $c_{p,sol}=300$ kg/m$^3$, $c_p^*=163$ kg/m$^3$, $H_{dis}=1$ mm, and $D_p=1.09\times10^{-10}$ m$^2$/s, by Eq. (11), $t_{dis}=203$ min. This disintegration time does not meet immediate-release specifications, and is far longer than the time to penetrate or disintegrate a single fiber 630. Thus if the concentration of polymer in (and the viscosity of) the solution 660 are too high, the drug release rate of the fibrous dosage form may be reduced substantially. This is detrimental to an immediate-release dosage form.

Figure 7:
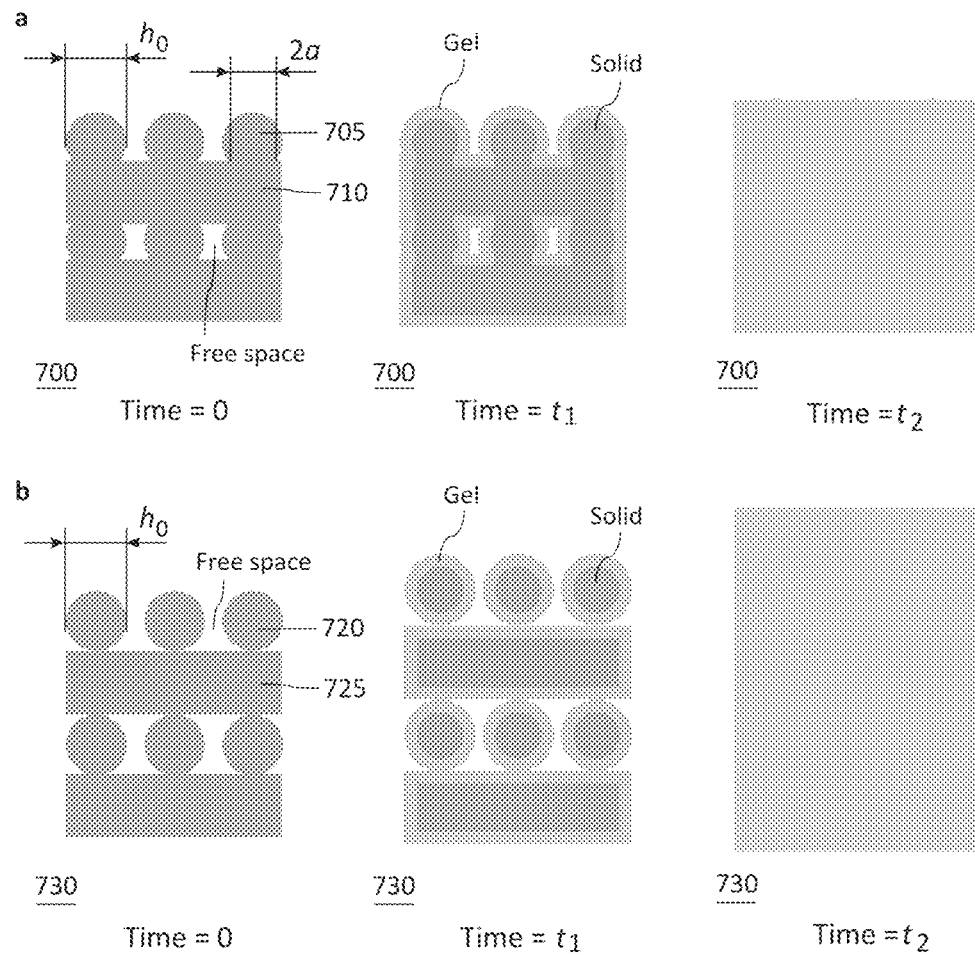
FIG. 7 shows expansion of structures with different contact widths between fibers after immersion in a dissolution medium.

It may be noted that in case the fibrous structure expands (and/or ruptures) after immersion in a dissolution medium, the relative amount of dissolution fluid in the solution 660 is increased. Thus the solution 660 is less concentrated and the threshold given by Eq. (9) can be increased. A parameter that affects expansion of the structure after immersion in a dissolution medium is the contact width between fibers or fiber segments, 2a. In FIG. 7a the contact width, 2a, between two fibers 705, 710, or two fiber segments 705, 710, is of the order of the initial fiber thickness, $h_0$. In this case, expansion of the structure 700 at times $t_1$ and $t_2$ after immersion of the structure 700 in a dissolution medium is minimal. If the contact width between fibers 720, 725 is substantially smaller than the initial fiber thickness, $h_0$, however, as shown in FIG. 7b, expansion of the structure 730 at times $t_1$ and $t_2$ after immersion of the structure 730 in a dissolution medium may be substantial.

Accordingly, for achieving a fibrous dosage form 600 that has the same (or a similar) disintegration rate as a single fiber 630 in a stagnant medium, the following parameters may be so selected that the fibers 630 do not interact and a gelated viscous mass is not formed: (a) the volume fraction of fibers 630, $\varphi_f$, with respect to a representative control volume of the dosage form 600 (or the drug-containing solid 601), (b) the amount (or fraction) of the absorptive/swellable and/or soluble polymeric excipient in the solid fibers 630, (c) the disentanglement concentration of an absorptive/swellable and/or soluble polymeric excipient in the fibers, and (d) the contact width, 2a, between fibers.

In some embodiments, the above conditions (a)-(d) of the foregoing paragraph can be reduced to a single condition on the viscosity of the solution 660 formed after interdiffusion of dissolution fluid 610 and fibers 630. As detailed later, the viscosity of the solution 660 is thus no greater than about 500 Pa·s in some embodiments disclosed herein.

Any more models or examples of the disintegration of a fibrous dosage form in a stagnant fluid obvious to a person of ordinary skill in the art are all within the scope of this invention.

f) Dosage Form Disintegration in a Stirred Medium

Figure 8:
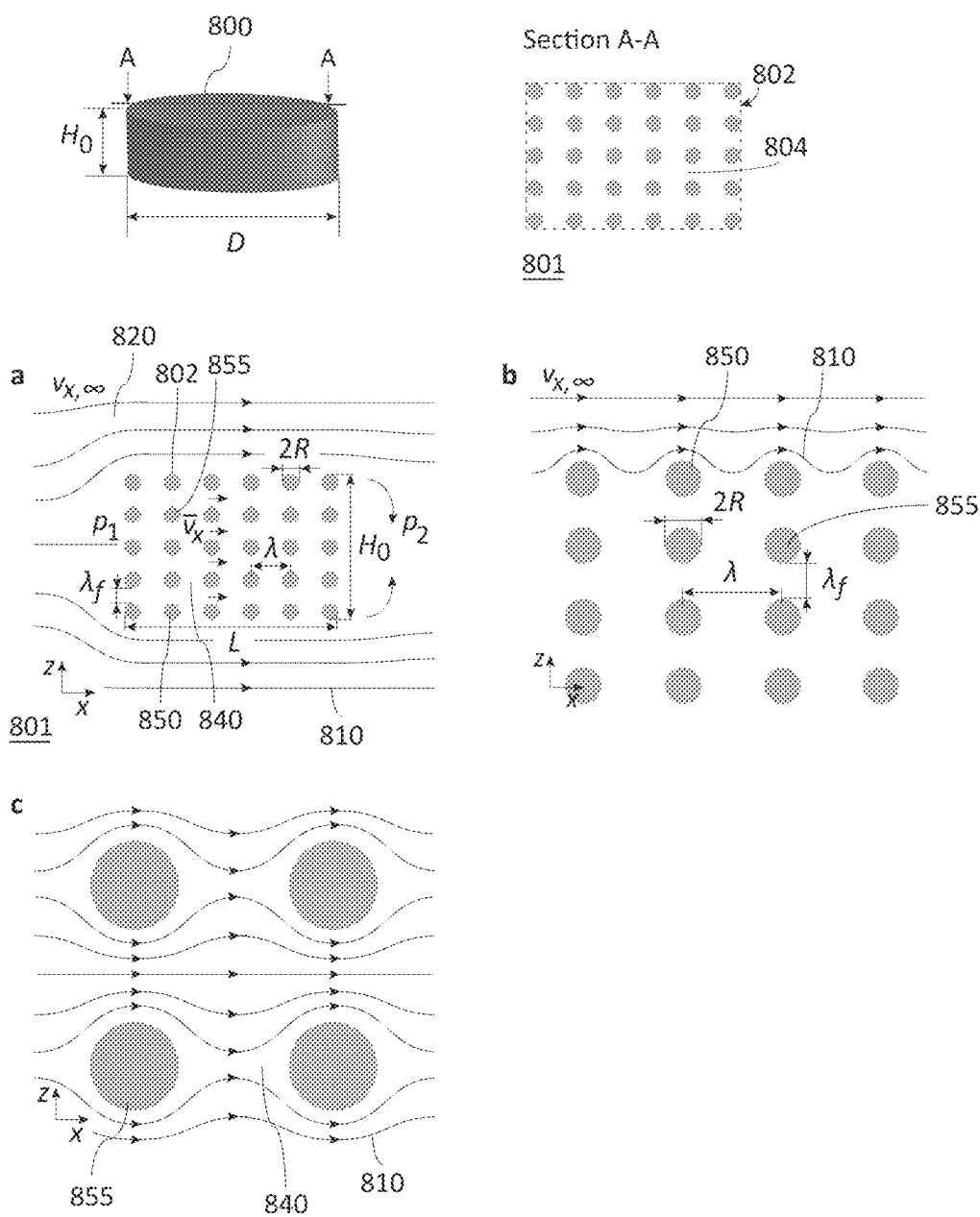
FIG. 8 illustrates schematics of fluid flow around and through a fibrous dosage form in a stirred dissolution fluid.

FIG. 8 presents a non-limiting example relevant to the disintegration of a fibrous dosage form in a stirred medium. The fibrous dosage form 800 comprises a drug-containing solid 801 having an outer surface 802 and an internal structure 804 contiguous with and terminating at said outer surface 802. The outer surface 802 may comprise a solid, or a liquid, or a gas, and is defined as the plane spanned by the fibers 855 (or fiber segments) at the surface 602 of the drug-containing solid 601. The internal structure 804 comprises a three dimensional structural network of fibers 850, 855. The fibers 850, 855 contain an active ingredient and a polymeric excipient that is erodible by a dissolution medium 820. The fibers 850, 855 further comprise fiber segments separated and spaced from adjoining segments by free spacings, $\lambda_f$, which define one or more free spaces 840 in the drug-containing solid 801.

FIG. 8a shows non-limiting examples of the streamlines 810 around the fibrous dosage form 800 in a stirred medium 820 with far-field velocity, $v_{x,\infty}$. The fluid velocity near the surface 802 is far greater than that in the interior 840. As a result, erosion of the fibers' surface planes is the greatest. If the inter-fiber spacing, $\lambda$, is much greater than the fiber diameter, 2R, the streamlines 810 bend around the fibers 850 and enter the space between them (FIG. 8b). They roughly follow the same paths as the ones near the surface of a single fiber in an infinite medium (FIG. 5g). Thus it may be assumed that the erosion rate of the exposed half (e.g., the "half fiber" of the exposed surface) equals that of a single fiber exposed to the same far-field velocity. For an initial fiber radius, $R_0$=250 µm, and a fluid velocity, $v_{x,\infty}$=10 mm/s, the erosion rate of a fiber on the dosage form surface for the parameter values given above may be derived from Eq. (7) as E=−dH/dt≈1087 nm/s. Accordingly, if surface erosion is from the two parallel faces of the dosage form 800, the time to erode 80 percent of a dosage form 800 that is 5 mm thick is: $t_{dis}$=0.8×H$_0$/2E ≈38 min. This is, however, longer than what is desired for a typical immediate-release dosage form.

(For further information on fluid flow and mass transfer around solid surfaces, see e.g., R. B. Bird, W. E. Stewart, E. N. Lightfoot, "Transport phenomena", $2^{nd}$ edn., John Wiley & Sons, 2002, or L. Rosenhead, "Laminar boundary layers", Oxford University Press, 1963).

Unlike the sequential layer-by-layer removal of material from the surface 802, material removal in the interior 840 of the dosage form is a parallel process because all the fibers 855 (e.g. the fibers in the interior) erode simultaneously. But the fibers 850, 855 impede fluid flow, reducing the fluid velocity in the interior of the structure (i.e., in the free spaces). The streamlines in the free spaces (or pores) may be as shown in FIG. 8c and an average fluid velocity in the free spaces, $\bar{v}_x$, may be approximated by Darcy's law:

$$\bar{v}_x = -\frac{1}{1-\phi_f}\frac{K}{\mu_l}\frac{dp}{dx} \qquad (12)$$

where $\mu_l$ is the viscosity of the liquid dissolution fluid, K is a hydraulic permeability and dp/dx a pressure gradient across the dosage form.

For a cross-ply arrangement of fibers as shown in FIG. 2, where fibers of volume per unit length $\pi R^2$ are arranged in spaces of volume per length $2R\lambda$, the hydraulic permeability, K, in the x-direction may be estimated as $$K = \frac{K_\perp + K_\parallel}{2} \qquad (13a)$$

where $$K_\perp = \frac{R\lambda}{2\pi}\left(\ln\left(\sqrt{\frac{2\lambda}{\pi R}}\right) - \frac{4-\pi^2(R/\lambda)^2}{8+2\pi^2(R/\lambda)}\right) \qquad (13b)$$

and $$K_\parallel = \frac{R\lambda}{16}\left(\frac{16}{\pi}\ln\left(\sqrt{\frac{2\lambda}{\pi R}}\right) + \frac{8R}{\lambda} - \frac{\pi R^2}{\lambda^2} - \frac{12}{\pi}\right) \qquad (13c)$$

(for further information, see, e.g., J. Happel and H. Brenner, "Low Reynolds number hydrodynamics with special application to particulate media", Prentice-Hall, Englewood Cliffs, N.J., 1965). Some estimated values of K, $\kappa_\perp$, and $K_\parallel$ are listed below for specific non-limiting examples of the radius of solid fibers, R, and the inter-fiber spacing, $\lambda$:

| | R (µm) | λ (µm) | $K_\perp$ (m$^2$) | $K_\parallel$ (m$^2$) | K (m$^2$) |
|---|---|---|---|---|---|
| B | 245 | 1783 | 2.2 × 10$^{-8}$ | 3.1 × 10$^{-8}$ | 2.7 × 10$^{-8}$ |
| C | 253 | 922 | 2.9 × 10$^{-9}$ | 4.1 × 10$^{-9}$ | 3.5 × 10$^{-9}$ |
| D | 243 | 629 | 4.6 × 10$^{-10}$ | 7.1 × 10$^{-10}$ | 5.9 × 10$^{-10}$ |

The pressure gradient across the dosage form 800 may be estimated from fluid flow outside the dosage form 800 (FIG. 8a). Far away from the dosage form 800, the dissolution fluid 820 is inviscid, at ambient pressure, and flowing towards the dosage form 800 at a velocity $v_{x,\infty}$. Near the front of the dosage form, however, the flow bifurcates, the streamlines 810 divide, and the fluid pressure increases. The relation between fluid pressure, p, and fluid velocity, $v_l$, in the free-flowing medium (outside the dosage form) may be described by Bernoulli's equation as p=p$_{atm}$+0.5 $\rho_l(v_{x,\infty}^2 - v_l^2)$ where $\rho_l$ is the density of the liquid medium. Thus if it is assumed that $v_f \approx 0$ at the front of the dosage form, the pressure at the front of the dosage form, $p_1$, is about $p_1 \approx p_{atm} + 0.5\, \rho_l\, v_{x,\infty}^2$.

Further assuming that $p \approx p_{atm}$ at the rear of the dosage form, the pressure gradient may be estimated as:

$$\frac{dp}{dx} \cong \frac{\Delta p}{L} \cong \frac{1}{2}\frac{\rho_l v_{x,\infty}^2}{L} \qquad (14)$$

where a cord length $L \approx D/2$ may be used for a dosage form that is of cylindrical disk shape (D is the dosage form diameter). Thus the average velocity of the fluid in the free spaces (or pores), $\bar{v}_x$, may be estimated by combining Eqs. (12)-(14).

If the pores are considered an array of tubes, the maximum fluid velocity in the pores (e.g., the free spaces) is a factor two greater than the average velocity, $\bar{v}_x$. Here we insert the maximum velocity as the fluid velocity, $v_\infty$, in Eq. (7) to calculate the erosion time of the fibers 855 in the interior of the three dimensional structural network. The following estimated velocities and erosion times, $t_E$, are obtained for the conditions under which the non-limiting experimental examples (shown later and summarized in Table 1) were performed:

|   | $R_0$ (μm) | $\lambda_0$ (μm) | $\bar{v}_x$ (μm/s) | $v_\infty$ (μm/s) | $t_E$ (min) | $t_{0.8}$ (min) |
|---|---|---|---|---|---|---|
| B | 245 | 1783 | 346 | 692 | 4.5 | 5.64 |
| C | 253 | 922 | 61 | 122 | 8 | 9.14 |
| D | 243 | 629 | 15 | 30 | 12 | 14.17 |

(Here again the calculations refer to a structure/arrangement/assembly as shown in FIG. 2. The parameter values $c_p^* = 163$ kg/m$^3$, $\rho_e = 1150$ kg/m$^3$, $D_p = 1.09 \times 10^{-10}$ m$^2$/s, $\rho_l = 1000$ kg/m$^3$, $\mu_l = 0.001$ Pa·s, $v_{x,\infty} = 10$ mm/s, and L=10 mm are used in combination with Eqns. (7) and (12)-(14). The values of the hydraulic conductivity, K, were assumed time-invariant in the calculations and are based on the initial radius, $R_0$, and the initial inter-fiber distance, $\lambda_0$. $t_{0.8}$ is the measured time to dissolve 80 percent of the drug content from the experimental dosage forms.)

The calculated $t_E$ values are well within immediate-release specification, and shorter than the times to disintegrate the dosage form structures from the exterior surfaces. Thus even though the velocity in the interior of the fibrous structure 804 is reduced substantially, material removal by simultaneous erosion of fibers 855 in the interior is faster than by sequential erosion from the surface in the non-limiting examples presented.

It may be noted, however, that even in a stirred medium, if swelling of fibers in the interior is faster than erosion, the fibrous dosage form may disintegrate as described in the non-limiting example e above. In this case, if expansion of the fibrous structure is unconstrained, the disintegration time of the structure is of the order of the penetration time, $t_{pen}$, of a single fiber (see, e.g., Eq. (6)). But if expansion of the structure is constrained, the dosage form structure may form a "viscous mass" after fiber swelling (for further details, see, e.g., the non-limiting examples (c) and (e) introduced above). Erosion of such a viscous mass would be mostly from the outer surface, which yields a much longer disintegration time than the simultaneous erosion of fibers 850, 855 with appreciable fluid flow through the interior of the structure (e.g., the internal structure 804).

As shown in the non-limiting example (e) introduced above, a small contact width allows the fibrous structure to more easily expand (or rupture) during the disintegration process. This may prevent the fibrous structure from forming a viscous mass that erodes slowly from its outer surfaces.

Finally, for a non-porous disk-shaped solid dosage form that erodes from both faces by convection (e.g., in a rotating basket of a USP dissolution apparatus), the erosion rate per eroding face may be approximated as:

$$E = -\frac{dH}{dt} = 0.62\left(\frac{D_p c_p^*}{\rho_e}\right)\left(\frac{\mu_l}{D_p \rho_l}\right)^{\frac{1}{3}}\left(\frac{\rho_l \Omega}{\mu_l}\right)^{\frac{1}{2}} \qquad (15)$$

where $\Omega$ is the angular velocity of the rotating basket. The effective disintegration time of the dosage form of initial thickness $H_0$ eroding from both faces is:

$$t_{dis} = \frac{H_0}{2}\frac{1}{dH/dt} \qquad (16)$$

(It may be noted that in the present non-limiting example, erosion from the sides is not considered because the thickness of the dosage form is assumed smaller than the dosage form width or length. Furthermore, we may note that the model may be adapted if the eroding surfaces are not planar.)

By way of example but not by way of limitation, if $c_p^* = 163$ kg/m$^3$, $D_p = 1.09 \times 10^{-10}$ m$^2$/s, $\rho_e = 1150$ kg/m$^3$, $\rho_l = 1000$ kg/m$^3$, $\mu_l = 0.001$ Pa·s, $\Omega = 5.24$ rad/s, and $H_0 = 5$ mm, by Eqs. (15) and (16) the calculated $0.8 \times t_{dis} = 73$ min. This estimation of the disintegration time is an order of magnitude greater than the values tabulated above for parallel erosion of fibers with flow through the fibrous structure. Thus also in a stirred medium, the fibrous structures are superior to the non-porous structures if immediate drug release is the goal.

(For further details related to the USP dissolution apparatus, see, e.g., The United States Pharmacopeial Convention, USP 39-NF 34; further details related to convective mass transfer models are given, e.g., in V. G. Levich, "Physicochemical Hydrodynamics", Prentice-Hall, Englewood Cliffs, N.J., 1962.)

Any more models or examples of the disintegration of a fibrous dosage form in a stirred fluid obvious to a person of ordinary skill in the art are all within the scope and spirit of this invention.

g) Summary of Disintegration Models

The above non-limiting models illustrate the effects of the following design parameters on the disintegration rate of fibers and fibrous dosage forms: the geometry of the three dimensional structural network of fibers, the solubility of the excipient in the dissolution medium (e.g., the "interfacial concentration"), the diffusivity of the excipient in the dissolution medium, the diffusivity of the medium in the excipient, the fractions of the individual components in the fibers, the contact width between fibers, and the disentanglement concentration of the excipient. All these parameters can be deterministically controlled during the manufacture of a fibrous dosage form.

Furthermore, the models illustrate that the fibrous dosage forms can be so designed that the length-scale of the disinegration-rate-determining mass transfer step is decreased from the thickness of the dosage form to the radius (or half-thickness) of the fiber. As a result, the fibrous dosage forms can be designed to deliver drug an order of magnitude faster than the corresponding non-porous solid forms. Thus the fibrous dosage forms offer predictable disintegration within a wide range of disintegration (and drug release) rates.

Dosage Form Design Features

In view of the theoretical models and considerations above, which are suggestive and approximate rather than exact, the design and embodiments of the fibrous dosage forms disclosed herein comprise the following.

The pharmaceutical dosage forms disclosed herein comprise a drug-containing solid having an outer surface and an internal structure contiguous with and terminating at said outer surface. The internal structure comprises a three dimensional structural network of one or more fibers. The fibers comprise at least one active ingredient, and in some cases also at least one excipient. The fibers further comprise fiber segments separated and spaced from adjoining fiber segments by free spacings, which define one or more free spaces in the drug-containing solid.

For achieving rapid percolation of dissolution fluid into the free spaces, in some embodiments a "free spacing", $\lambda_f$, (e.g., a "free" distance between adjoining (i.e., neighboring) fibers, or adjoining fiber segments, or adjoining assembled drug-containing structural elements that are zero-dimensional or one-dimensional or two-dimensional) is such that the percolation time of physiological/body fluid into one or more interconnected free spaces of the dosage form is no greater than 900 seconds under physiological conditions. This includes, but is not limited to percolation times no greater than 700 seconds, no greater than 500 seconds, no greater than 300 seconds, no greater than 100 seconds, no greater than 50 seconds, or no greater than 10 seconds under physiological conditions. The pressure of the physiological/body fluid at different surfaces of the interconnected free spaces may assume different values during fluid percolation.

Figure 9:
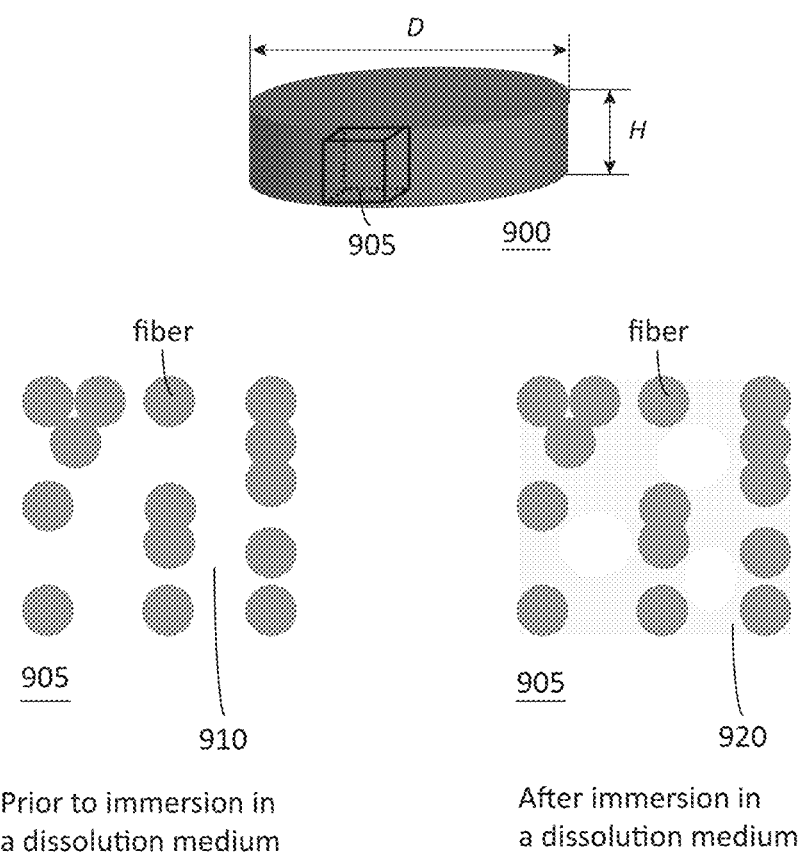
FIG. 9 presents a non-limiting example of percolation of dissolution medium into an interconnected free space.

By way of example but not by way of limitation, the percolation time into one or more interconnected free spaces of the dosage form may be determined as follows (FIG. 9). First a volume 905 of the dosage form 900 may be identified that contains one or more interconnected free spaces 910. Then the volume of the interconnected free spaces 910 in said volume of the dosage form 905 may be determined. Then said volume of the dosage form 905 may be immersed in a dissolution medium. Then the volume of dissolution medium 920 that percolated into the volume of the interconnected free spaces 910 of said volume of the dosage form 905 may be determined. As soon as the volume of dissolution medium 920 that percolated into the volume of the interconnected free spaces 910 of said volume of the dosage form 905 is greater than 20 percent of the initial volume of the interconnected free spaces 910, the volume of the interconnected free spaces 910 of said volume of the dosage form 905 may be considered percolated.

Figure 10:
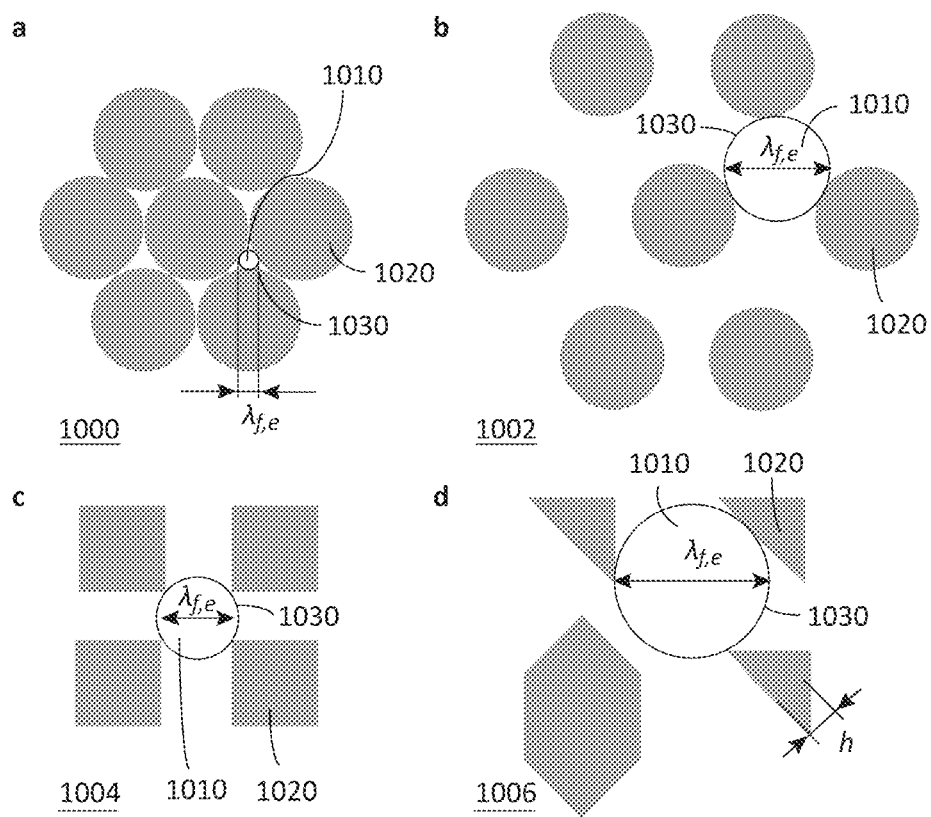
FIG. 10 shows schematics of the microstructure of solid dosage forms according to this invention to illustrate the 'effective free spacing' between adjoining fibers or fiber segments.

Also, in some embodiments, the effective free spacing, $\lambda_{f,e}$, on average is greater than 0.1 µm. This includes, but is not limited to an average $\lambda_{f,e}$ greater than 0.25 µm, or greater than 0.5 µm, or greater than 1 µm, or greater than 2 µm, or greater than 5 µm, or greater than 7 µm, or greater than 10 µm, or greater than 15 µm, or greater than 20 µm, or greater than 25 µm, or greater than 30 µm, or greater than 40 µm, or greater than 50 µm, or in the ranges of 0.1 µm-5 µm, 0.1 µm-3 mm, 0.25 µm-5 mm, 0.5 µm-5 mm, 0.25 µm-3 mm, 0.1 µm-2.5 mm, 0.25 µm-2 mm, 1 µm-4 mm, 5 µm-4 mm, 10 µm-4 mm, 15 µm-4 mm, 20 µm-4 mm, 30 µm-4 mm, 40 µm-4 mm, or 50 µm-4 mm. As shown in the non-limiting 2-D examples 1000, 1002, 1004, 1006 of FIG. 10, the "effective free spacing" between adjoining fiber segments is defined as the maximum diameter of a sphere that fits in the corresponding free space 1010 considering the fibers 1020 as rigid, fixed bodies. The diameter of such spheres may be estimated from 2-d images of the microstructure. Such 2-d images may be obtained from scanning electron micrographs of the cross section of the dosage form. The greatest circles 1030 that fit in the free spaces 1010 of the microstructure may be drawn on the scanning electron micrograph (e.g., the 2-d image) and the area-based average diameter of the circles 1030 (e.g., the average effective free spacing) calculated.

Figure 11:
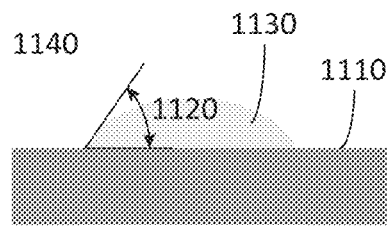
FIG. 11 illustrates a schematic of the contact angle of a fluid droplet on a surface.

Furthermore, in some embodiments at least one of the one or more excipients is wettable by a physiological/body fluid under physiological conditions. In the context of this work, a solid surface 1110 is wettable by a fluid if the contact angle 1120 of a fluid droplet 1130 on the solid surface 1110 exposed to air 1140 is no more than 90 degrees (FIG. 11). In some embodiments, the contact angle may not be stationary. In this case, in the invention herein a solid surface is wettable by a fluid if the contact angle 1120 of a fluid droplet 1130 on the solid surface 1110 exposed to air 1140 is no more than 90 degrees at least 60-360 seconds after the droplet 1130 has been deposited on the surface.

If the fibers (or segments of the same fiber) are not bonded to each other and/or if bonding is just at a point and/or a small local area of dimension smaller than the inter-fiber spacing, the free spaces are open and interconnected. In case, however, that some or all of the drug-containing fibers are bonded to another fiber over a length of the order of (or greater than) the inter-fiber spacing, closed clusters (or even closed individual cells) defining one or more free spaces may exist. In a closed cluster or a closed individual cell, the free space is entirely surrounded (i.e., enclosed) by walls comprising the drug containing solid.

Figure 12:
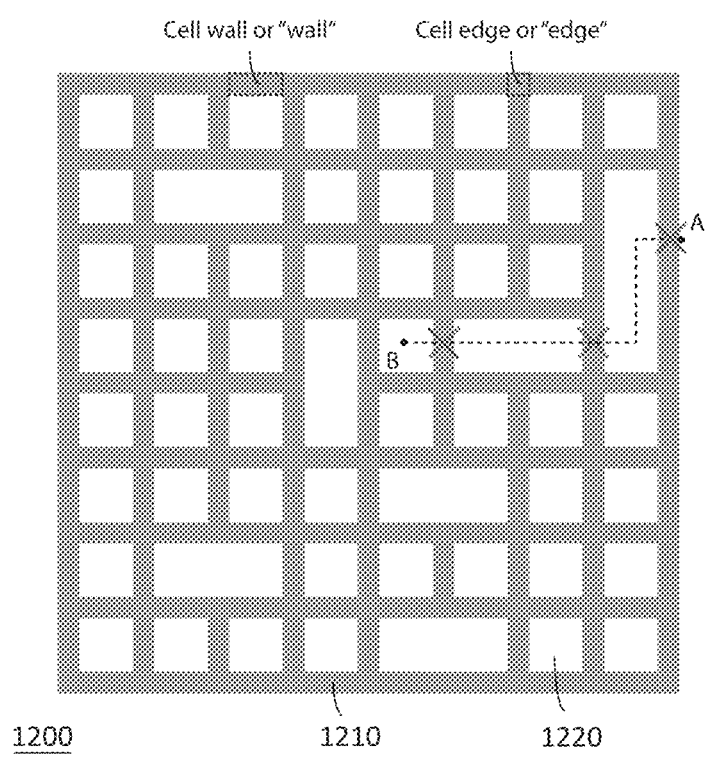
FIG. 12 depicts a schematic diagram of the microstructure of solid dosage forms according to this invention to illustrate the number of walls that must be ruptured to obtain an interconnected cluster of free space that extends from the outer surface of the drug-containing solid to a point in the interior.

In some embodiments disclosed herein, the following holds. If the average wall thickness is greater than 100 µm, an interconnected, continuous cluster of free space that extends from the outer surface of the drug-containing solid to a given point in the internal structure is obtained if no more than 0 to 12 walls are ruptured (e.g, walls of drug-containing solid enclosing free space are opened or removed). This includes, but is not limited to 0-11, 0-10, 0-9, 0-8, 0-7, 0-6, or 0-5 walls that must be ruptured to obtain an interconnected cluster of free space that extends from the outer surface to a given point in the internal structure. If the average wall thickness is smaller than 100 µm, no more than 0 to 24 walls must be ruptured to obtain such an interconnected cluster of free space. This includes, but is not limited to 0-22, 0-22, 0-18, 0-16, 0-14, 0-12, or 0-10 walls that must be ruptured to obtain an interconnected cluster of free space that extends from the outer surface of the drug-containing solid to a given point in the interior. In FIG. 12, a 2-d example without limitation 1200 is presented that shows 3 walls 1210 to be ruptured for obtaining an interconnected cluster of free space 1220 from point A to point B.

For achieving a specific surface area (i.e., surface area-to-volume ratio) large enough to guarantee rapid fiber disintegration, in some embodiments the one or more fibers have an average thickness, $h_0$, no greater than 2.5 mm. This includes, but is not limited to $h_0$ no greater than 2 mm, or no greater than 1.5 mm. It may be noted, however, that if the fibers are very thin and tightly packed, the inter-fiber spacing and free spacing between the fibers can be very small, too. This may limit the rate at which dissolution fluid can percolate or flow through the fibrous structure upon immersion in a dissolution fluid. Thus, in some embodiments the one or more fibers have an average thickness, $h_0$, in the ranges of 0.1 μm-2.5 mm, 0.5 μm-2.5 mm, 1 μm-2.5 mm, 1.75 μm-2.5 mm, 2.5 μm-2.5 mm, 2.5 μm-2 mm, 5 μm-2 mm, 10 μm-2 mm, 15 μm-2.5 mm, 20 μm-2.5 mm, 30 μm-2.5 mm, 40 μm-2.5 mm, or 50 μm-2.5 mm. We may further note that the average thickness of the fibers, $h_0$, can be greater than 2.5 mm in dosage forms that release drug over longer periods of time (e.g., in a time greater than about 25-45 minutes).

Figure 13:
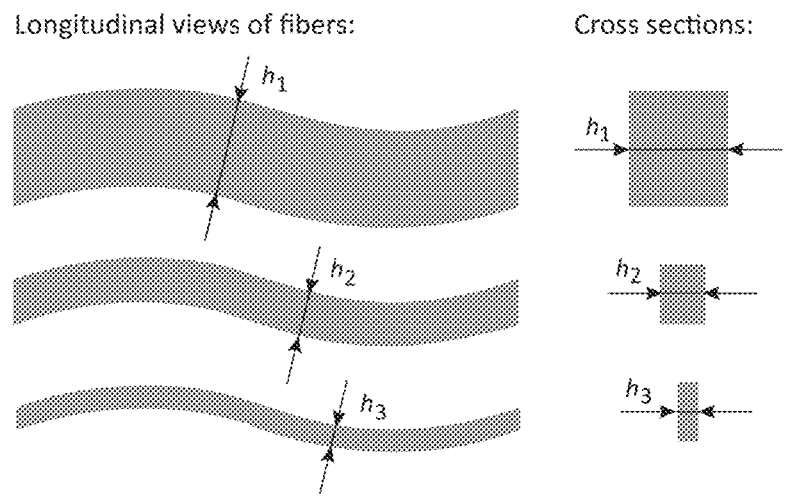
FIG. 13 presents three fibers of different thickness.

The fiber thickness, h, may be considered the smallest dimension of a fiber (i.e., h≤w and h≤l, where h, w and l are the thickness, width and length of the fiber, respectively). The average fiber thickness, $h_0$, is the average of the fiber thickness along the length of the one or more fibers. By way of example but not by way of limitation, FIG. 13 presents three fibers of equal length but different thicknesses. In this non-limiting example, the average fiber thickness, $h_0=(h_1+h_2+h_3)/3$. Both the average fiber thickness, $h_0$, and the thickness of a specific fiber at a specific position, h, may, for example, be derived from scanning electron micrographs of the cross section of the dosage form.

Furthermore, in some embodiments, a contact width, 2a, between two fibers (or two fiber segments) is no greater than 2.5 mm. This includes, but is not limited to a contact width between two fibers (or two fiber segments) no greater than 2 mm, or no greater than 1.75 mm, or no greater than 1.5 mm. In other examples without limitation, a contact width, 2a, between two fibers (or two fiber segments) may be no greater than 1.1 times the thickness of the contacting fibers (or fiber segments) at the position of the contact. This includes, but is not limited to a contact width, 2a, between two fibers (or two fiber segments) no greater than 1 time, or no greater 0.8 times, or no greater than 0.6 times the thickness of the contacting fibers (or fiber segments) at the position of the contact.

In case one or more fibers (or fiber segments) are bonded together to form a 0-dimensional, or a 1-dimensional, or a 2-dimensional structural element (or a "wall"), the average thickness of the assembled structural element (or the wall) may be no greater than 2.5 mm in some embodiments disclosed herein. By way of example but not by way of limitation, this includes assembled structural elements or walls with thickness no greater than 2 mm, or in the ranges of 0.1 μm-2.5 mm, 0.25 μm-2.5 mm, 0.5 μm-2.5 mm, 2 μm-2.5 mm, 2.5 μm-2 mm, 1 μm-2 mm, 0.5 μm-1.5 mm, or 2 μm-2 mm. The average thickness of a two-dimensional structural element is referred to as the average of the thickness along the length and width of the element. The average thickness of a one-dimensional structural element is referred to as the average of the thickness along the length of the element. The average thickness of a zero-dimensional structural element is referred to as the thickness of the element (e.g., the smallest dimension of the element).

Moreover, we may note that the cross section of a fiber (and also the cross section of a 0-dimensional, 1-dimensional, or 2-dimensional structural element) may, for example, be polygonal, ellipsoidal, etc. (or combinations thereof), and it may comprise inward-curved or outward-curved or un-curved surfaces. Furthermore, the cross section of a fiber (or an assembled structural element) may vary along the length of the fiber (or the assembled structural element).

A fiber or a fiber segment in the three dimensional structural network of one or more fibers may, for example, be defined by its position (e.g., the position of its central axis or the pathway of the line formed by its central axis) relative to a reference point or frame. (In the invention herein, a reference frame may be understood as a reference coordinate system.) The reference point or the origin and orientation of the reference frame may be specified on the outer surface or within the internal structure of the drug containing solid.

In some embodiments of the invention herein, the position of at least one fiber or at least one fiber segment in the three dimensional structural network of one or more fibers is precisely controlled. Such embodiments include, but are not limited to three dimensional structural networks of one or more fibers wherein the position of a fraction of the fibers or fiber segments is precisely controlled. The volume fraction of fibers or fiber segments (with respect to the total volume of fibers or fiber segments that make up the three dimensional structural network of one or more fibers) of which the position is precisely controlled can be greater than 0.1, or greater than 0.3, or greater than 0.5, or greater than 0.7, or greater than 0.9. It may be noted that in the context of the invention herein, a variable or a parameter (e.g., the position of a fiber, or an inter-fiber spacing, or a fiber thickness) is precisely controlled if it is deterministic and not stochastic (or random). A variable or parameter may be deterministic if, upon multiple repetitions of a step that includes said variable, the standard deviation of the values of said variable is smaller than the average value. This includes, but is not limited to a standard deviation of the values of said variable smaller than half the average value, or smaller than one third of the average value, or smaller than a quarter of the average value, or smaller than one fifth or the average value, or smaller than one sixth of the average value of said variable.

In some embodiments, furthermore, at least one inter-fiber spacing, λ, and/or at least one fiber thickness, h, is/are precisely (or deterministically) controlled. Thus, in some embodiments herein, if a fiber is produced multiple times under identical conditions, the standard deviation of the thickness of said fibers is less than the average value of said fibers' thickness. Similarly, if an inter-fiber spacing is produced multiple times under identical conditions, the standard deviation of said inter-fiber spacing is less than the average value of said inter-fiber spacing in certain embodiments of the invention herein. It may be noted that in the invention herein, an inter-fiber spacing includes, but is not limited to a spacing between two fiber segments. Also, we may note that the inter-fiber spacing between fibers or fiber segments may change along the length of said fibers or fiber segments. Similarly, a fiber thickness includes, but is not limited to the thickness of a fiber segment. Also, the thickness of a fiber or a fiber segment may change along the length of said fiber or fiber segment.

A non-limiting example of a three dimensional structural network of one or more fibers wherein the position of a large fraction (or all) of the fibers, the inter-fiber spacing, and the fiber thickness are controlled (or precisely controlled) is an ordered structure. As shown in the non-limiting schematics of FIGS. 2, 3, and 4, such regular or ordered structures can, for example, comprise multiple layers of fibers or fiber segments that are stacked. The fibers or fiber segments in a layer can be oriented parallel (or almost parallel) to each other in some non-limiting ordered structures herein. The advantage of ordered structures over disordered or random structures is that the properties, such as the drug release rate by the structure, can be better controlled.

Moreover, as shown in FIGS. 2 and 3, in some embodiments herein the three dimensional structural network of one or more fibers may comprise inter-fiber contacts (e.g., contacts between fibers and/or fiber segments). Such inter-fiber contacts include, but are not limited to point contacts (as schematically shown in FIGS. 2a and 3c) or line contacts as schematized in FIGS. 3a, 3d and 3e (for further information related to point contacts and line contacts, see, e.g., K. L. Johnson, "Contact mechanics", Cambridge University Press, 1985). The inter-fiber contacts may provide mechanical support to the fibrous structure (e.g., the three dimensional structural network of one or more fibers). They may, however, also hold up disintegration and dissolution of the fibrous structure upon immersion in a dissolution medium. Thus, in some embodiments the number of inter-fiber contacts in a fibrous dosage form, and/or at least one position of an inter-fiber contact in a fibrous dosage form, and/or a contact width of at least one inter-fiber contact in a fibrous dosage form is/are precisely controlled in the three dimensional structural network of one or more fibers. This includes, but is not limited to embodiments wherein the position of a fraction of the inter-fiber contacts is precisely controlled, said fraction being greater than 0.3 or greater than 0.5. This further includes, but is not limited to embodiments wherein the contact width of a fraction of the inter-fiber contacts is precisely controlled, said fraction being greater than 0.3 or greater than 0.5.

Typically, the volume fraction of drug-containing fibers in the dosage form is no greater than 0.98. In other non-limiting examples, the volume fraction of drug-containing fibers in the dosage form is no greater than 0.95, no greater than 0.93, or no greater than 0.9. In most cases, it is in the range 0.1-0.9, depending on how the one or more fibers are arranged. A small volume fraction of drug containing fibers is desirable to fill small amounts of drug in a comparable large volume (i.e., if the dosage form is used for delivery of a highly potent drug with a drug dose of just a few milligrams or less). On the contrary, a large volume fraction of drug-containing fibers is desirable to fill large amounts of drug in a small volume (i.e., if the dosage form is used for delivery of a low potency drug or delivery of multiple active ingredients with a total drug dose of several 100 mg or more).

For achieving rapid erosion of fibers after contact with physiological/body fluids, in some embodiments the drug-containing fibers include at least one excipient that has a solubility greater than 0.1 g/l in physiological/body fluids under physiological conditions. This includes, but is not limited to a solubility of at least one excipient in a physiological/body fluid greater than 0.5 g/l, or greater than 1 g/l, or greater than 5 g/l, or greater than 10 g/l, or greater than 20 g/l, or greater than 30 g/l, or greater than 50 g/l, or greater than 70 g/l, or greater than 100 g/l. Furthermore, the diffusivity of a dissolved excipient molecule in a physiological/body fluid may be greater than $1 \times 10^{-12}$ m²/s under physiological conditions. This includes, but is not limited to a diffusivity of a dissolved excipient molecule in a physiological/body fluid greater than $2 \times 10^{-12}$ m²/s, greater than $4 \times 10^{-12}$ m²/s, greater than $6 \times 10^{-12}$ m²/s, greater than $8 \times 10^{-12}$ m²/s, or greater than $1 \times 10^{-11}$ m²/s under physiological conditions. The volume fraction of soluble excipient in the excipient (e.g., the excipient in its totality or all the volume of the one or more excipients in the one or more fibers) may be greater than 0.02. This includes, but is not limited to volume fractions of the soluble excipient in the excipient greater than 0.04, greater than 0.06, greater than 0.08, or greater than 0.1.

In polymers that form viscous solutions when combined with a dissolution medium, the 'solubility' in the context of this invention is the polymer concentration in physiological/body fluid at which the average shear viscosity of the polymer-physiological/body fluid solution is 5 Pa·s in the shear rate range 1-100 l/s under physiological conditions. The pH value of the physiological/body fluid may thereby be adjusted to the specific physiological condition of interest. By contrast, the solubility of a material that does not form a viscous solution when combined with a dissolution medium is the maximum amount of said material dissolved in a given volume of dissolution medium at equilibrium divided by said volume of the medium. It may, for example, be determined by optical methods.

Furthermore, in some embodiments the drug-containing fibers include at least one excipient that is absorptive of a physiological/body fluid. The effective diffusivity of physiological/body fluid in an absorptive excipient (and/or a fiber) is greater than $0.5 \times 10^{-11}$ m²/s under physiological conditions. In other examples without limitation, the effective diffusivity of physiological/body fluid in an absorptive excipient (and/or a fiber) may be greater than $1 \times 10^{-11}$ m²/s, greater than $3 \times 10^{-11}$ m²/s, greater than $6 \times 10^{-11}$ m²/s, or greater than $8 \times 10^{-11}$ m²/s under physiological conditions.

Alternatively, for absorptive excipients where diffusion of physiological/body fluid to the interior is not Fickian, a rate of penetration may be specified. In some embodiments, the rate of penetration of a physiological/body fluid into a solid, absorptive excipient (and/or a fiber) is greater than an average thickness of the one or more drug-containing fibers divided by 3600 seconds (i.e., $h_0/3600$ μm/s). In other examples without limitation, rate of penetration may be greater than $h_0/1800$ μm/s, greater than $h_0/1200$ μm/s, greater than $h_0/800$ μm/s, or greater than $h_0/600$ μm/s.

For determining the effective diffusivity (and/or the rate of penetration) of dissolution medium in a solid, absorptive excipient (and/or a fiber) the following procedure may be applied. A fiber (e.g a fiber of the dosage form structure or a fiber that just consists of the absorptive excipient) may be fixed at both ends and placed in a still dissolution medium at 37° C. The time $t_1$ for the fiber to break apart or deform substantially may be recorded. (By way of example but not by way of limitation, a deformation of a fiber may be considered substantial if either the length, width, or thickness of the fiber differs by more than 10 to 20 percent from its initial value. In fibers with weight fraction, $w_e$, or volume fraction, $\varphi_e$, of absorptive/swellable excipient smaller than 0.4, a deformation of a fiber may be considered substantial if either the length, width, or thickness of the fiber differs by more than $25 \times \varphi_e$ percent or $25 \times w_e$ percent from its initial value.) The effective diffusivity, $D_{eff}$, may then be determined according to $D_{eff} = h_f^2/4t_1$ where $h_f$ is the initial fiber thickness (e.g., the thickness of the dry fiber). Similarly, the rate of penetration of a physiological/body fluid into the fiber is equal to $h_f/2t_1$.

The effective diffusivity of dissolution medium in or the average velocity at which the fluid front advances (i.e., the rate of penetration of a physiological/body fluid) into a solid, absorptive excipient (or a fiber) may also be determined by spectral methods. By way of example but not by way of limitation, a film with thickness of the order of the thickness of a fiber may be cast from the fiber material (or the absorptive excipient only) by either addition and removal of a solvent or by melting and solidification. One side of the film may be exposed to the dissolution medium. On the other side of the film, the concentration of dissolution medium may be monitored. As soon as the monitored concentration of dissolution medium raises substantially (e.g., as soon as the concentration of water or dissolution fluid in the absorptive/swellable excipient on the monitored surface is greater than twice the concentration of water or dissolution fluid in the absorptive/swellable excipient of the initial solid film or fiber), the film is penetrated. The time $t_1$ to penetrate the film may be recorded and the effective diffusivity and rate of penetration calculated as detailed in the previous paragraph. Spectral methods are suited for materials that have some mechanical strength (i.e., increased viscosity) when they are penetrated by the dissolution fluid. They are also suited for materials (or fibers) where the deformation of the fiber upon penetration of dissolution fluid is small.

In some embodiments, at least one excipient of the drug-containing solid transitions from solid to a fluidic or gel consistency solution upon being solvated with a volume of physiological/body fluid equal to the volume of the one or more free spaces of the drug-containing solid (or dosage form). To ensure that the disintegration rate of such a drug-containing solid is of the order of the disintegration rate of a single fiber (e.g., to avoid that the drug-containing solid forms a viscous mass upon immersion in a dissolution medium that erodes slowly from its outer surfaces), the viscosity of said solution is no greater than 500 Pa·s. In other words, a solution comprising the weight of soluble/absorptive excipient in the drug-containing solid and a volume of physiological/body fluid equal to the volume of the free spaces of the drug-containing solid (specifically the volume of the free spaces that are removable by the dissolution fluid), has a viscosity no greater than 500 Pa·s. This includes, but is not limited to a viscosity of said solution less than 400 Pa·s, less than 300 Pa·s, less than 200 Pa·s, less than 100 Pa·s, less than 50 Pa·s, less than 25 Pa·s, or less than 10 Pa·s. In the context of this work, the viscosity of a solution is the average shear viscosity of the solution in the shear rate range 1-100 l/s under physiological conditions.

Non-limiting examples of excipients that if used at the right quantities satisfy some or all of the above requirements include polyethylene glycol (PEG), polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, butylmethacrylat-(2-dimethylaminoethyl)methacrylat-methylmathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, hydroxypropyl methylcellulose), starch, polylactide-co-glycolide, polyvinyl caprolactam-polyvinyl acetate-polyethylene glycol graft copolymer, pregelatinized starch, lactose, sodium starch glycolate, polyacrylic acid, acrylic acid crosslinked with allyl sucrose or allyl pentaerythritol (e.g., carbopol), or polyols (e.g., lactitol, maltitol, mannitol, isomalt, xylitol, sorbitol, maltodextrin, etc.), among others.

The one or more free spaces may be filled with a matter selected from the group comprising solid, liquid, gas (or vacuum), or combinations thereof. If one or more fibers (or one or more segments of a fiber) is/are partially or entirely surrounded by free space, the content of said free space may be removed partially or entirely after contact with dissolution fluid to give the fluid access to the fibers. This condition is, for example, satisfied by gases. Examples of biocompatible gases that may fill the free space include air, nitrogen, $CO_2$, argon, oxygen, and nitric oxide, among others.

Liquids that are partially or entirely removed from the structure upon contact with dissolution fluid, and thus may be used to fill the free spaces include, but are not limited to such biocompatible low viscosity fluids as: Polyethylene glycol (PEG) with molecular weight smaller than about 1000 Da (e.g. PEG 400, PEG 300, etc.), Poloxamer 124, 2-Pyrrolidone, Glycerol triacetate (Triacetin), D-alpha tocopheryl polyethylene glycol 1000 succinate (TPGS), Polyoxyl Hydroxystearate, Polyoxyl 15 Hydroxystearate, Castor oil, Polyoxyl castor oil (Polyethoxylated castor oil), Polyoxyl 35 castor oil, Polyoxyl hydrogenated castor oil, Glyceryl monooeleate, Glycerin, Propylene glycol, Propylene carbonate, Propionic acid, Peanut oil, water, Sesame oil, Olive oil, Almond oil, combinations of such (and/or other) liquids with a polymer or any other molecule that dissolves in them, among others.

Non-limiting examples of solids that are removed or dissolved after contact with physiological/body fluid include sugars or polyols, such as Sucrose, Lactose, Maltose, Glucose, Maltodextrin, Mannitol, Maltitol, Isomalt, Lactitol, Xylitol, Sorbitol, among others. Other examples of solids include polymers, such as polyethylene glycol, polyvinyl pyrrolidone, polyvinyl alcohol, among others. Other examples of solids include effervescent agents, such as sodium bicarbonate. The relevant physical properties of a solid that is bonded to a drug-containing fiber are high solubility and diffusivity in physiological/body fluids to ensure its rapid removal after contact with physiological/body fluid. Thus other non-limiting examples of a solid include solid active pharmaceutical ingredients with high solubility and diffusivity, such as Aliskiren. Typically, a solid material should have a solubility in physiological/body fluid under physiological conditions greater than 50 g/l to be removed or dissolved rapidly after contact with dissolution medium. This includes, but is not limited to a solubility greater than 75 g/l, or greater than 100 g/l, or greater than 150 g/l. The diffusivity of the solid material (as dissolved molecule in physiological/body fluid under physiological conditions) should typically be greater than $4 \times 10^{-12}$ m$^2$/s if the solid material must be dissolved rapidly after contact with dissolution medium. This includes, but is not limited to a diffusivity greater than $6 \times 10^{-12}$ m$^2$/s, or greater than $8 \times 10^{-12}$ m$^2$/s, or greater than $1 \times 10^{-11}$ m$^2$/s.

Furthermore, one or more filler materials such as microcrystalline cellulose or others, one or more sweeteners, one or more taste masking agents, one or more stabilizing agents, one or more preservatives, one or more coloring agents, or any other common or uncommon excipient may be added as excipient to the dosage form.

In some embodiments, a disintegration time of the dosage form (or the drug-containing solid) is no greater than 45 minutes. This includes, but is not limited to a disintegration time no greater than 30 minutes, no greater than 25 minutes, no greater than 20 minutes, or no greater than 15 minutes. In the context of this disclosure, the disintegration time is defined as the time required to release 80 percent of the drug content of a representative dosage form structure into a stirred dissolution medium. The released drug may be a solid, such as a solid drug particle, and/or a molecule, such as a dissolved drug molecule. The disintegration test may, for example, be conducted with a USP disintegration apparatus under physiological conditions. (See, e.g. The United States Pharmacopeial Convention, USP 39-NF 34). Another method without limitation to conduct a disintegration test is by a USP basket apparatus (i.e., a USP apparatus 1 as shown in The United States Pharmacopeial Convention, USP 39-NF 34) under physiological conditions (e.g., at a temperature of 37° C. and at a stirring rate or basket rotation rate of 50-150 rpm). In this method, the time to disintegrate 80 percent of the representative dosage form structure after immersion in the stirred dissolution medium may, for example, be determined by visual or other optical methods. It may be noted that if the drug is in molecular form immediately or almost immediately after it is released from the dosage form structure, the disintegration time is about the same as the time to dissolve 80% of the drug content of a representative dosage form structure after immersion in a stirred dissolution medium.

In case the drug containing fibers are well bonded to each other (or to a solid material that fills the one or more free spaces), the greater of a tensile strength or a yield strength of the assembled dosage form material is no less than 0.005 MPa. In other examples without limitation, the greater of a tensile strength or a yield strength of the assembled dosage form material is no less than 0.01 MPa, or 0.015 MPa, or 0.02 MPa, or 0.025 MPa, or 0.04 MPa, or 0.06 MPa, or 0.1 MPa, or 0.25 MPa, or 0.5 MPa. Bonding between the drug containing fibers (or between the fibers and the content of the free space) can, for example, be by interdiffusion of molecules, mechanical interlocking, or by other forces due to the surface energy of the materials. In some embodiments, good bonding is achieved without deforming the drug containing fibers plastically in the solid state. In this case, it may be possible to readily distinguish the fibers from the free spaces in an image of the cross section of the dosage form (e.g., a scanning electron micrograph, a computerized tomograph, an x-ray image, or an image taken by another technique).

Figure 14:
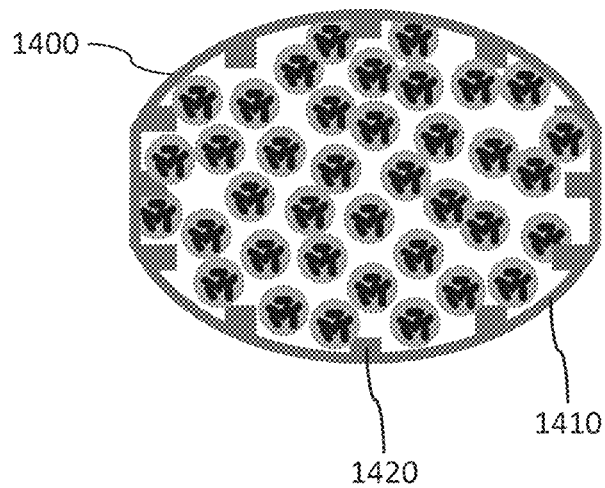
FIG. 14 is a schematic diagram of the microstructure of a coated solid dosage form according to this invention.

In some embodiments, the mechanical properties of the three dimensional structural networks of one or more fibers disclosed herein (particularly the structures with weakly bonded fibers (or fiber segments), or even not bonded or unbonded fibers (or fiber segments)) may be improved, for example, by applying a coating on the surface of the dosage form (or the outer surface of the drug-containing solid). The thickness of the coating may, for example, be non-uniform. In the non-limiting example of FIG. 14, the coating 1400 comprises "thick" rings 1410 that provide mechanical support and "thin" sheets 1420 that disintegrate rapidly after the dosage form is immersed in a dissolution medium. In other non-limiting embodiments, the coating thickness may be uniform. We may note that a capsule encapsulating the dosage form (or the drug-containing solid) may also be considered a coating. Furthermore, it may be noted that in some embodiments of the invention disclosed herein, a coating may serve as taste masking agent, protective coating, means of providing color to the dosage form, enteric coating, means of improving the aesthetics of the dosage form, or have any other common or uncommon function of a coating. Moreover, in some non-limiting examples of the invention herein, a coating may be applied on the fibers of the three dimensional structural network of fibers.

Also the coating materials include, but are not limited to polyethylene glycol (PEG), polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, butylmethacrylat-(2-dimethylaminoethyl)methacrylat-methylmathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, hydroxypropyl methylcellulose), starch, polylactide-co-glycolide, polyvinyl caprolactam-polyvinyl acetate-polyethylene glycol graft copolymer, pregelatinized starch, lactose, sodium starch glycolate, or polyacrylic acid, Sucrose, Lactose, Maltose, Glucose, Maltodextrin, Mannitol, Maltitol, Isomalt, Lactitol, Xylitol, Sorbitol, a sweetener, a coloring agent, a preservative, a stabilizer, a taste masking agent, among others.

Figure 15:
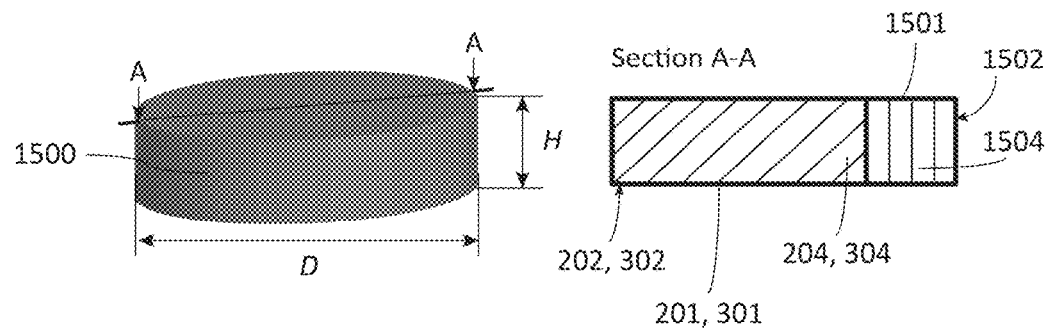
FIG. 15 presents a dosage form comprising at least two drug-containing solids.

In some embodiments, in addition to the drug-containing solid 201, 301 described above, the dosage form 1500 disclosed herein may comprise another drug-containing solid 1501 that contains at least one active ingredient (or one or more other drug-containing solids that contain at least one active ingredient; all such other drug-containing solids are referred to here as "other solid" or "other drug-containing solid"). Said other drug-containing solid 1501 has an outer surface 1502 and internal structure 1504 contiguous with and terminating at said outer surface 1502 as shown in FIG. 15. In some embodiments, 80 percent of the other solid's 1501 drug content is converted to dissolved molecules in a time greater than 60 minutes after immersion of the dosage form in a physiological/body fluid under physiological conditions. In other embodiments, 80 percent of the other solid's 1501 drug content is converted to dissolved molecules in a time no greater than 60 minutes after immersion of the dosage form in a physiological/body fluid under physiological conditions.

EXPERIMENTAL EXAMPLES

The following examples set forth, in detail, ways by which the fibrous dosage forms may be prepared and analyzed, and will enable one of skill in the art to more readily understand the principle thereof. The following examples are presented by way of illustration and are not meant to be limiting in any way.

Example 1: Preparation of Melt-Processed Dosage Forms

Figure 16:
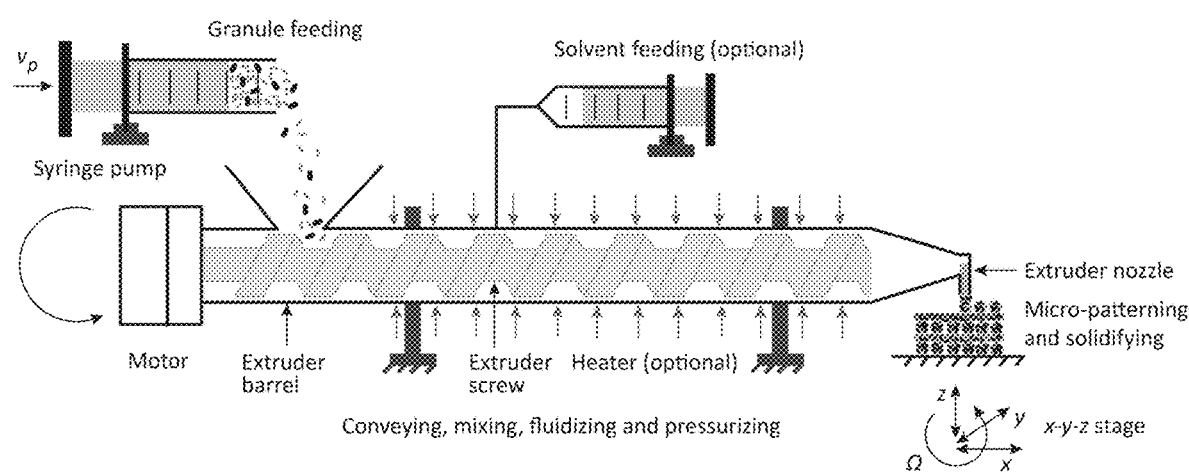
FIG. 16 is a schematic of a process and apparatus to manufacture the fibrous dosage forms disclosed herein.

Melt-processed dosage forms were prepared by first mixing 40 wt % of solid Acetaminophen particles (particle size about 40-80 µm as received from Sigma, St. Louis) with 60 wt % granules of polyethylene glycol with a molecular weight of 35,000 g/mol (PEG 35k, as received from Sigma, St. Louis). The solid mixture was then loaded into the granule-feeding unit of an adapted extrusion-micropatterning machine as shown schematically in FIG. 16. The granule-feeding unit was set to deliver 1.7 mg/s of the drug and excipient material into the extruder barrel of the adapted extrusion-micropatterning machine. The rotation rate of the extruder screw was about 3-5 rpm and the temperatures of the extruder barrel and nozzle were set to 80° C.

Melt-processed fibrous dosage forms were then micropatterned as follows. A single-layer pattern of the fibrous effluent from the extruder nozzle was first deposited on a surface (also referred to herein as "moving platform" or "linear stage" or "x-y-z stage") which was moved along the desired path in the x-y plane. Further patterns were then added layer-by-layer to the deposited structure until the deposited fibrous structure reached the desired thickness. The velocity of the linear stage in the x-y plane was 7.3 mm/s during deposition (or patterning). The distance between the nozzle exit and the top of the deposited fibrous structure (or the deposition surface) was kept at 1 to 2 mm during patterning. The ambient temperature and that of the x-y-z stage were at room temperature. The process was stopped as soon as the thickness of the dosage form reached about 5 mm. Three different three dimensional structural networks of fibers were prepared: structures of the configuration shown in FIG. 2 with a nominal fiber radius, $R_n$=250 µm (equal to the inner radius of the extruder nozzle) and a nominal inter-fiber distance in a single layer, $\lambda_n$, of either 1750, 900, or 600 µm ($\lambda_n$ is determined by the path of the x-y-z stage). In addition to the fibrous structures, single fibers of nominal radius, $R_n=250$ μm, were prepared by solidification of the fibrous effluent from the extruder nozzle. The position and velocity of the linear stage, and the velocity and radius (e.g. the half thickness) of the fibrous extrudate were precisely controlled during the process.

For preparing melt-processed minimally-porous solid dosage forms, a stainless steel mold was placed on the top surface of the linear stage and was filled with the effluent extrudate until a height of 5 mm was reached. The material was left in the mold, which was kept at room temperature, for about 2 minutes to solidify. Subsequently, the solid dosage form was ejected.

The elastic modulus and mechanical strength of the fibrous and minimally-porous dosage forms was sufficient to handle the dosage forms without taking specific care.

Example 2: Preparation of Wet-Processed Dosage Forms

Wet-processed dosage forms were prepared by first mixing 60 wt % of solid ibuprofen particles (particle size about 20-40 μm, as received from BASF, Ludwigshafen, Germany) with 40 wt % particles of polyvinyl alcohol-polyethylene glycol graft copolymer 3:1 with a molecular weight of 45,000 Daltons (particle size about 50 μm, as received from BASF, Ludwigshafen, Germany; tradename: Kollicoat IR). The particles were mixed and loaded into the granule-feeding unit of an adapted extrusion-micropatterning machine as shown schematically in FIG. 16. The granule-feeding unit was set to deliver 1.7 mg/s (of the drug-excipient material) into the extruder barrel of the adapted extrusion-micropatterning machine. The liquid-feeding unit (e.g., the solvent-feeding unit) of the extrusion-micropatterning machine was filled with deionized water and set to deliver a water flow rate of 1.1 μl/s into the extruder barrel. The rotation rate of the extrusion screw was about 3-5 rpm.

For preparing wet-processed fibrous dosage forms, a single layer of the fibrous effluent from the extruder nozzle was micro-patterned on a moving surface (e.g., a "linear stage" or "x-y-z stage") as described in the example 1 above. Then further patterns were added layer-by-layer to the deposited structure (e.g., the layers were stacked) until the deposited fibrous structure reached the desired thickness. The x-y-z stage (and the deposited structure) were position- and velocity-controlled. The velocity of the x-y-z stage was 14.4 mm/s during deposition of the material. The distance between the nozzle exit and the top of the fibrous structure (or the deposition surface defined by the x-y-z stage) was kept at 1 to 2 mm during patterning. The process was stopped when the thickness of the dosage form reached about 4-5 mm. After that warm air at a temperature of 60° C. was blown on the dosage form structure for about 5 minutes to dry the fibrous material. The fibrous dosage forms prepared had a three dimensional structural network of fibers as schematically shown in FIG. 2. The nominal fiber radius of the dosage form structure, $R_n=250$ μm (as given by the inner radius of the extruder nozzle), and the nominal fiber-to-fiber spacing in a single layer, $\lambda_n=900$ μm. In addition to the fibrous dosage forms, single fibers were prepared by drying the fibrous effluent from the extruder nozzle as above.

For preparing wet-processed minimally-porous solid dosage forms, a stainless steel mold was placed on the top surface of the linear stage and was filled with the effluent stream until a height of about 4-5 mm was reached. The material was then left in the mold for about 48 hours in a dry environment at room temperature to remove the residual water. Subsequently, the dosage form was ejected from the mold.

Example 3: Dosage Form Microstructures

Figure 17:
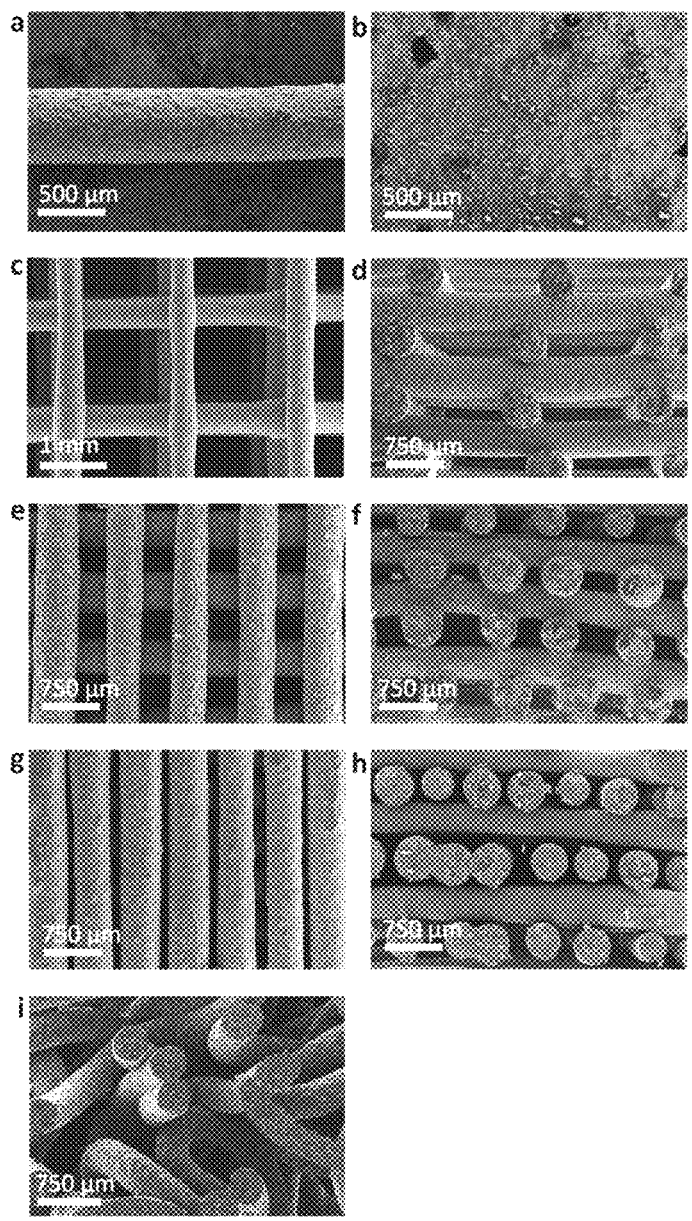
FIG. 17 depicts scanning electron microscopy (SEM) images of dosage forms according to this invention.

FIG. 17 presents scanning electron microscopy (SEM) images of example microstructures of melt-processed fibers and dosage forms. FIG. 17a is the image of a single fiber with drug particles embedded in an excipient matrix. The diameter of the fiber is roughly 539 μm (as listed in Table 1), slightly greater than the inner diameter of the nozzle exit. FIG. 17b is the microstructure of an essentially non-porous solid dosage form with drug particles embedded in an excipient matrix. FIGS. 17c-17h are microstructures of the fibrous dosage forms. The structures are ordered. Also, the fiber radius, R, and the inter-fiber distance, λ, are predictable and agree well with the nominal parameters set by the inner radius of the extruder nozzle and the path of the x-y-z stage as summarized in Table 1. FIG. 17i shows a wet-processed fibrous structure with random or almost random (e.g., not ordered) assembly/arrangement of the fibers. This structure was obtained if the distance between the nozzle exit and the top of the fibrous layer (or the deposition surface defined by the linear stage) was increased to about 15 mm.

Example 4: Fiber and Dosage Form Disintegration

For imaging melt-processed dosage form and fiber disintegration, the dosage forms and fiber were first attached to a sample holder using a drop of Loctite Super Glue. The sample holder was then immersed in the dissolution fluid which was a 0.05 M phosphate buffer solution (prepared with sodium phosphate monobasic and sodium phosphate dibasic) at a pH of 5.8 and at 37° C. (as suggested by the monograph of The United States Pharmacopeial Convention, USP 39-NF 34). For imaging dosage form disintegration, the fluid was stirred with a paddle rotating at 50 rpm during the entire dosage form disintegration time and images were captured at specific time points. Images of the disintegrating fibers were captured in both a stirred medium as above and also in a still (not stirred) dissolution fluid. All the images of dosage form disintegration were taken with a Nikon DX camera equipped with an additional 7 diopters of magnification.

Figure 18:
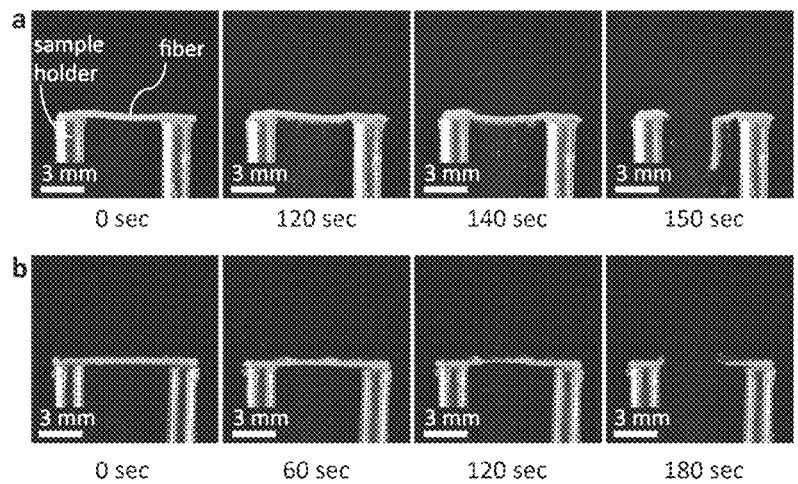
FIG. 18 displays disintegration of melt-processed fibers in both stagnant and stirred dissolution fluid.

Representative images that present the disintegration processes of melt-processed single fibers (i.e., fibers consisting of 60% PEG 35k and 40% Acetaminophen) in still and stirred dissolution fluid are shown in FIG. 18. FIG. 18a is the series of images of a single fiber in stagnant (not stirred) medium. Soon after immersion of the fiber in the fluid, a viscous layer surrounding the fiber developed. The layer grew with time and starting at 60-90 seconds after immersion, small fragments fell downwards from the fiber (the density of the viscous layer (and the fiber) were slightly greater than that of water, and hence the viscous layer was flowing downwards due to gravity). Furthermore, at about 100-135 seconds after immersion, the fiber had deflected downwards by about 100-300 μm from its initial position. At a time $t_1 \approx 150$ seconds, the fiber broke away from its support and fell down. (The fiber radius remained roughly constant during the entire process shown suggesting that the radial expansion due to fiber swelling is roughly compensated by the removal of material from the fiber into the dissolution fluid). An effective diffusivity of dissolution medium in a fiber may be estimated as $D_{eff}=R^2/t_1=(269.5\times10^{-6})^2/150=4.8\times10^{-10}$ m²/s (269.5 μm is the initial radius of a wet-processed fiber). Similarly, a rate of penetration of dissolution medium into a fiber is about $R/t_1=269.5/150$ µm/s=1.8 µm/s.

Images of the disintegration process of a melt-processed single fiber in stirred dissolution medium are shown in FIG. 18b. Here also a viscous layer that surrounded the fiber developed soon after immersion. But unlike in the previous case, the radius of the fiber decreased continuously with time until the fiber disappeared about 150 seconds after immersion (e.g., the viscous layer is continuously sheared away by convection in the stirred medium).

Figure 19:
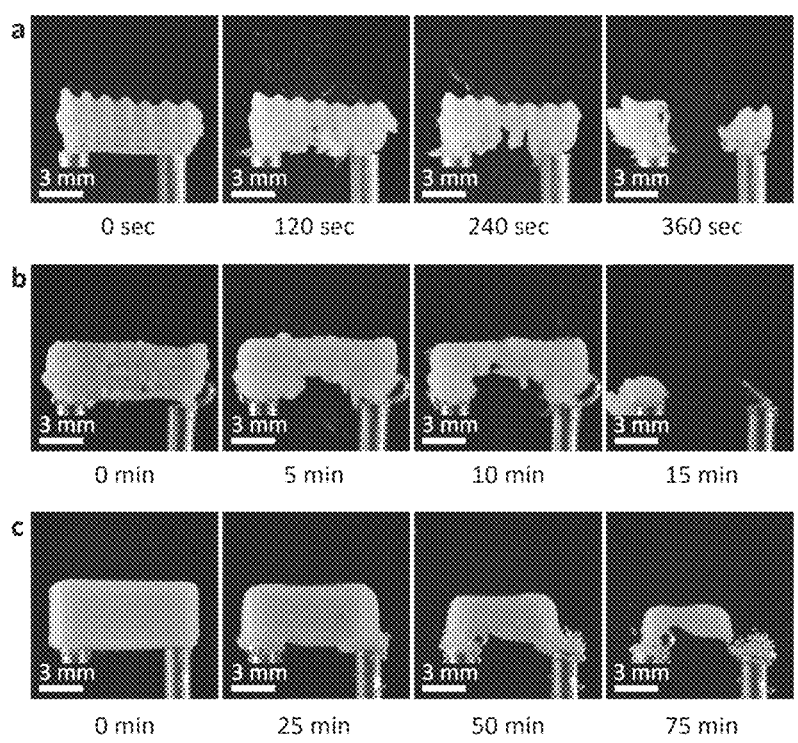
FIG. 19 presents disintegration of melt-processed dosage forms according to this invention in stirred dissolution fluid.

FIG. 19 presents selected images of melt-processed fibrous and non-porous dosage forms during disintegration in a stirred medium. The disintegration of a dosage form with $R/\lambda=0.14$ (i.e., a volume fraction of fibers, $\varphi_f=0.22$) is shown in FIG. 19a. Immediately after immersion in the dissolution medium, the void spaces (or free spaces) of the structure were filled with the fluid. The fibrous microstructure then started to transition from clear to diffuse. At the same time, fluidized material was removed from the structure until it finally disappeared. The disintegration time of the dosage form increased by about a factor of two compared with the single fiber. Images of the disintegration of a fibrous dosage form with $R/\lambda=0.39$ ($\varphi_f=0.61$) are presented in FIG. 19b. As in the previous case, after immersion of the dosage form, the void spaces were filled with fluid, the solid phase transitioned from clear to diffuse (e.g., from solid or solid-like to fluidic or fluid-like), and the fluidized material was then removed from the dosage form. The time to disintegrate the dosage form, however, increased by about a factor of 2-3 compared with the fibrous assembly with smaller $R/\lambda$ (or $\varphi_f$) shown in FIG. 16a.

FIG. 19c illustrates disintegration of the melt-processed non-porous solid dosage form. The dosage form eroded continuously from the top and bottom surfaces. The disintegration time of this dosage form was more than a factor ten greater than that of the fibrous dosage form with $\varphi_f=0.22$.

Figure 20:
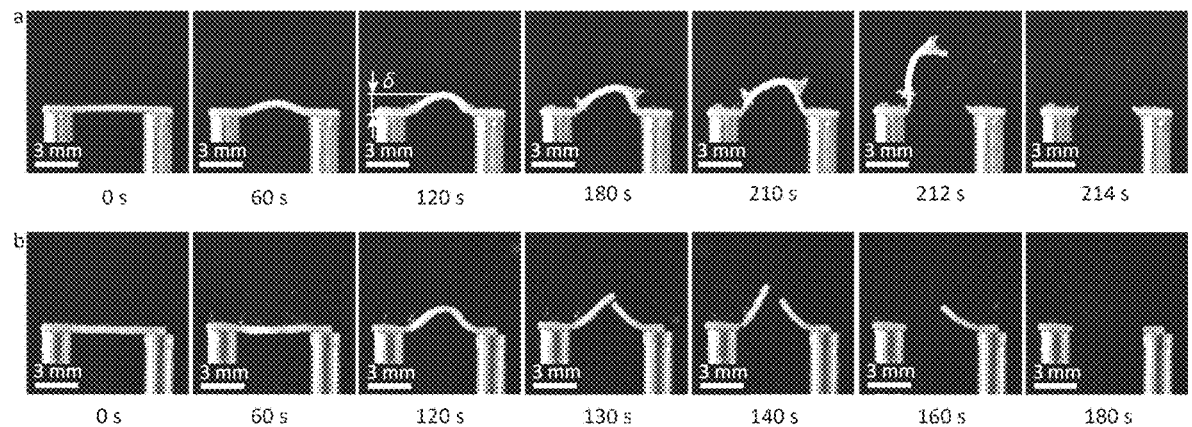
FIG. 20 shows disintegration of wet-processed fibers in both stagnant and stirred dissolution fluid.

The disintegration process of a wet-processed single fiber (i.e., a fiber consisting of 60% ibuprofen and 40% polyvinyl alcohol-polyethylene glycol graft copolymer with molecular weight ~45,000 Da) in still (i.e., unstirred) dissolution medium is shown in FIG. 20a. The dissolution fluid was a 0.05 M phosphate buffer solution (prepared with sodium phosphate monobasic and sodium phosphate dibasic) at a pH of 7.2 and at 37° C. Soon after immersion of the fiber in the fluid, a viscous layer surrounding the fiber developed. The viscous layer grew in thickness with time, and so did the fiber radius (and length, i.e., which is why the fibers bent and buckled with time). Some small fragments of the viscous layer, however, were removed from the fiber as the layer grew. Furthermore, starting at about 30-60 seconds after immersion, the fiber bent upwards and deflected from its initial position. The displacement increased with time. The maximum displacement, δ, reached about one third of the initial fiber length at a time $t_1=120$ seconds after immersion. Thus the fiber length at $t_1=120$ s is about $1/\cos(\text{atan}(2/3))$ =1.2 times the initial fiber length. The fiber has therefore deformed substantially at this time and an effective diffusivity of dissolution medium in a fiber may be estimated as $D_{eff}=R^2/t_1=(200\times10^{-6})^2/120 \text{ m}^2/\text{s}=3.3\times10^{-10} \text{ m}^2/\text{s}$ (200 µm is the initial radius of a wet-processed fiber). Similarly, a rate of penetration of dissolution medium into a fiber is about $R/t_1=200/120$ µm/s=1.7 µm/s.

FIG. 20b presents selected images of the disintegration of a wet-processed single fiber in stirred medium. Again, a viscous layer surrounding the fiber developed, and starting at 30-90 seconds after immersion the fiber bent upwards and deflected from its initial position. Then at about 130 seconds, the fiber broke in half, and at 140-180 seconds both halfs broke away from the support. The fiber radius decreased slightly within the experimental time frame. Thus more material was removed from the fiber in the stirred medium than in the unstirred medium.

Before the disintegration of wet-processed dosage forms was imaged, the edges of the dosage form were cut away so that the microstructural topology was uniform across the entire structure. Imaging of the disintegration of wet-processed dosage forms and fibers was done the same way as the melt-processed dosage forms.

Figure 21:
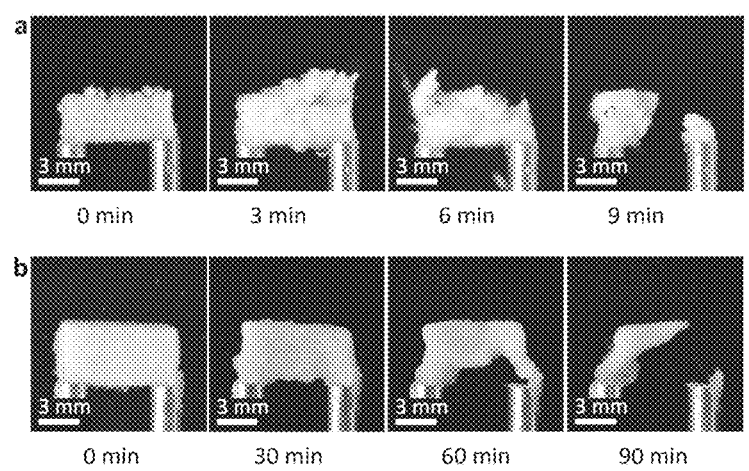
FIG. 21 presents disintegration of wet-processed dosage forms according to this invention in stirred dissolution fluid.

The disintegration of a wet-processed fibrous dosage form with $R/\lambda=0.27$ (i.e., a volume fraction of fibers, $\varphi_f=0.42$) is shown in FIG. 21a. Immediately after immersion in the dissolution medium, the void spaces (i.e., the free spaces) of the structure were filled with the fluid. The fibrous microstructure then started to transition from clear to diffuse (e.g., from solid or solid-like to fluidic or fluid-like). At the same time, fluidized material was removed from the structure. Furthermore, fibrous elements or small assemblies of such elements broke away from the dosage form until it disintegrated. The disintegration time of the dosage form was about a factor of 2-3 greater than that of the single fiber.

FIG. 21b illustrates disintegration of the wet-processed minimally-porous solid dosage form. The dosage form eroded continuously from the top and bottom surfaces. The disintegration time, however, increased by more than a factor of ten compared with the fibrous dosage form with $\varphi_f=0.42$.

Example 5: Drug Release

Drug release (and drug dissolution) from fibers and dosage forms was tested by a USP dissolution apparatus 1 (as shown, e.g., in The United States Pharmacopeial Convention, USP 39-NF 34) filled with 900 ml of the dissolution fluids above (a 0.05 M phosphate buffer solution with pH 5.8 for melt-processed fibers and dosage forms and pH 7.2 for wet-processed fibers and dosage forms. The temperature of the dissolution fluid was 37±2° C. in both cases). The basket was rotated at 50 rpm. The concentration of dissolved drug in the dissolution fluid was measured versus time by UV absorption at 244 nm using a fiber optic probe. For all the dosage forms, the fraction of drug dissolved increased steadily with time at roughly constant rate until it plateaud out to the final value.

Figure 22:
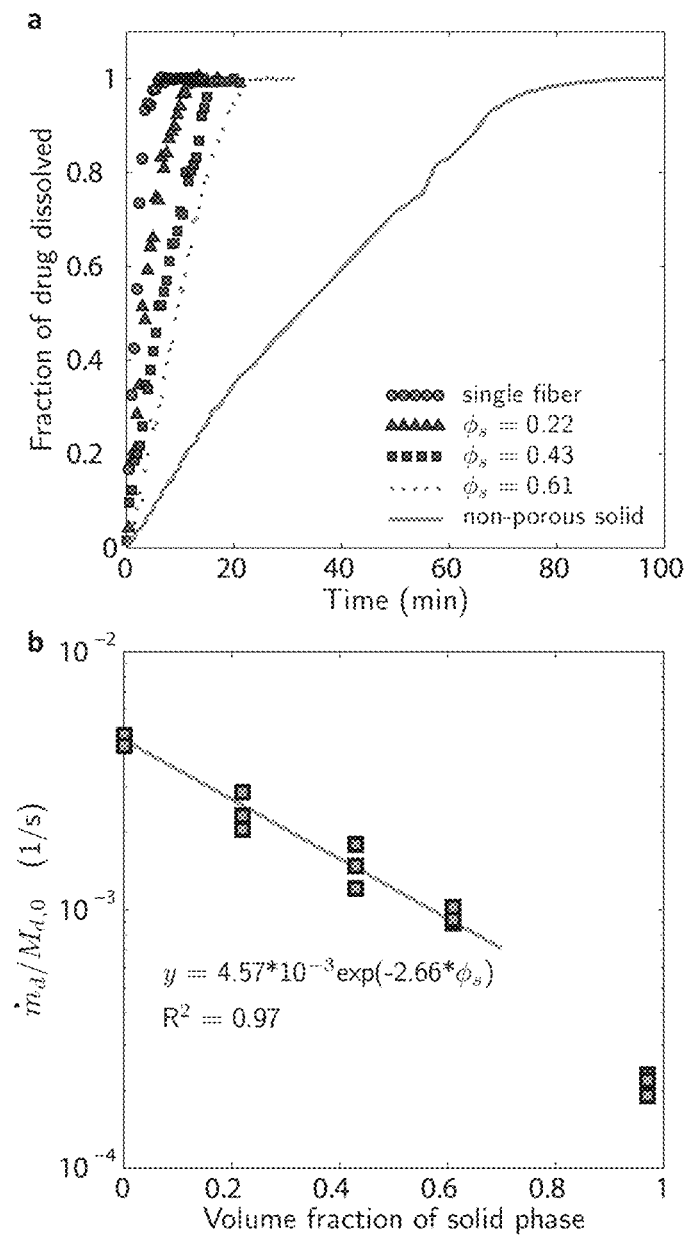
FIG. 22 displays the results of the fraction of drug dissolved versus time of melt-processed dosage forms according to this invention.

FIG. 22a presents representative curves of the fraction of drug dissolved versus time of the melt-processed fibrous dosage forms together with the data of a single fiber and the drug release results of the non-porous solid structure. The time to dissolve 80% of the drug content, $t_{0.8}$, can thus be readily extracted from these curves. The average $t_{0.8}$ values of the various dosage forms tested are listed in Table 1. The average $t_{0.8}$ of the single fiber is roughly 2.9 mins. $t_{0.8}$ increases if the fibers are assembled to a dosage form and the volume fraction of solid is increased, to 5.64 mins for the dosage form with $\varphi_f=0.22$, and to about 14.2 mins if $\varphi_f=0.61$. $t_{0.8}$ of the fibrous dosage forms, however, is much faster than the drug release time of the corresponding non-porous solid structure with $t_{0.8}=63$ mins.

Figure 23:
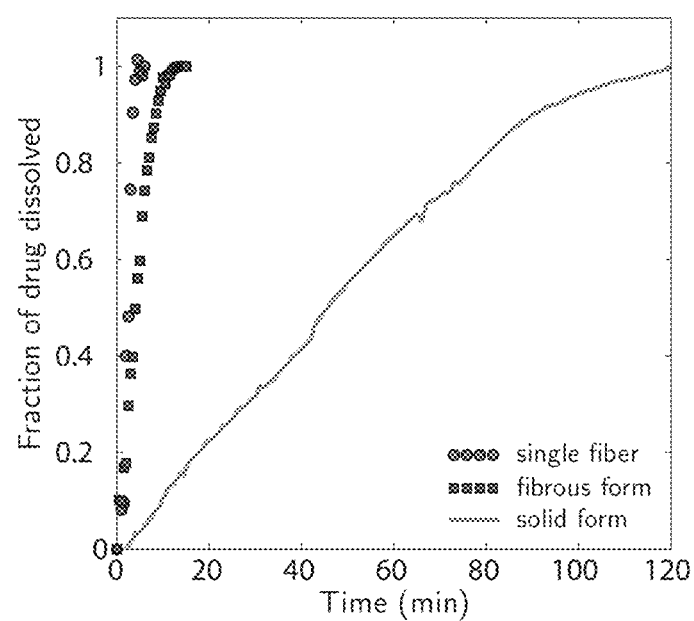
FIG. 23 shows the results of the fraction of drug dissolved versus time of wet-processed dosage forms according to this invention.

FIG. 22b presents the fraction of drug dissolved per unit time, i.e., $1/M_{d,0}\times dm_d/dt$ ($=0.8/t_{0.8}$), versus volume fraction of the solid phase (e.g., the volume fraction of fibers; $M_{d,0}$ is the initial amount of drug in the dosage form, $dm_d/dt$ the drug dissolution rate, and $t_{0.8}$ the time to dissolve 80% of the drug content). The data of the fibrous dosage forms can be fitted to an exponential curve. The $1/M_{d,0} \times dm_d/dt$ values of the solid dosage forms, however, do not follow this curve and are substantially smaller than predicted by the fit equation FIG. 23 shows representative curves of the fraction of drug dissolved versus time of the wet-processed fibrous dosage forms together with the data of a wet-processed

TABLE 1

Summary of microstructural parameters and drug dissolution times of single fibers, fibrous dosage forms, and non-porous solid dosage forms.

| | $2R_n$ (μm) | 2R (μm) | $\lambda_n$ (μm) | $\lambda$ (μm) | $R_n/\lambda_n$ | $R/\lambda$ | $\varphi_{f,n}$ | $\varphi_f$ | $t_{0.8}$ (min) |
|---|---|---|---|---|---|---|---|---|---|
| A | 500 | 539 | — | — | — | — | 0.0+ | 0.0+ | 2.89 |
| B | 500 | 490 ± 55 | 1750 | 1783 ± 47 | 0.14 | 0.14 | 0.22 | 0.22 | 5.64 |
| C | 500 | 505 ± 34 | 900 | 922 ± 38 | 0.28 | 0.27 | 0.44 | 0.43 | 9.14 |
| D | 500 | 485 ± 25 | 600 | 629 ± 70 | 0.42 | 0.39 | 0.65 | 0.61 | 14.17 |
| E | — | — | — | — | — | — | — | — | 63.00 |
| F | 500 | 408 ± 11 | 900 | — | — | — | 0.0+ | 0.0+ | 3.00 |
| G | 500 | 404 ± 68 | 900 | 745 ± 76 | 0.31 | 0.27 | 0.49 | 0.42 | 7.00 |
| H | 500 | — | — | — | — | — | — | — | 79.00 |

A: melt-processed single fiber;
B, C, D: melt-processed fibrous dosage forms;
E: melt-processed minimally-porous solid dosage form;
F: wet-processed single fiber;
G: wet-processed fibrous dosage form;
H: wet-processed minimally-porous solid dosage form
The nominal fiber radius, $R_n$, is the inner diameter of extruder nozzle.
The nominal fiber-to-fiber distance, $\lambda_n$, is determined by the path along which the fiber is deposited.
The measured fiber radius, R, and fiber-to-fiber distance, $\lambda$, are obtained from SEM images of the cross section of the dosage form. Non-limiting examples of such images are shown in FIG. 17.
$t_{0.8}$ is the time to dissolve 80% of the drug contained in the dosage form. It is derived from the results of drug release experiments shown in FIGS. 22 and 23.
According to Eq. (1a), $\varphi_f = \pi R/2\lambda$.

single fiber and the drug release results of wet-processed minimally-porous solid structure. The time to dissolve 80% of the drug content, $t_{0.8}$, is readily extracted from these curves. The average $t_{0.8}$ values of the various dosage forms tested are listed in Table 1. The average $t_{0.8}$ of the single fiber is roughly 3 mins. $t_{0.8}$ increases if the fibers are assembled to a dosage form, to 7 mins. $t_{0.8}$ of the fibrous dosage forms, however, is much faster than the drug release time of the corresponding minimally-porous solid structure with $t_{0.8}$=79 mins.

Example 6: Viscosities of PEG 35k-Water Solutions

The shear viscosities of PEG 35k-physiological/body fluid solutions was determined by first mixing water with PEG 35k at a polymer concentration of 5, 10, 20, 33, and 47 wt % (i.e., the water weight fractions were 95, 90, 80, 67, and 53 wt %). A shear rheometer (TA Instruments, ARG2 Rheometer, stress-controlled) equipped with a 60 mm diameter cone with an apex angle of 178° was used. The temperature was 37±1° C. during the experiments, and the shear strain-rate range was 1-100/s.

Figure 24:
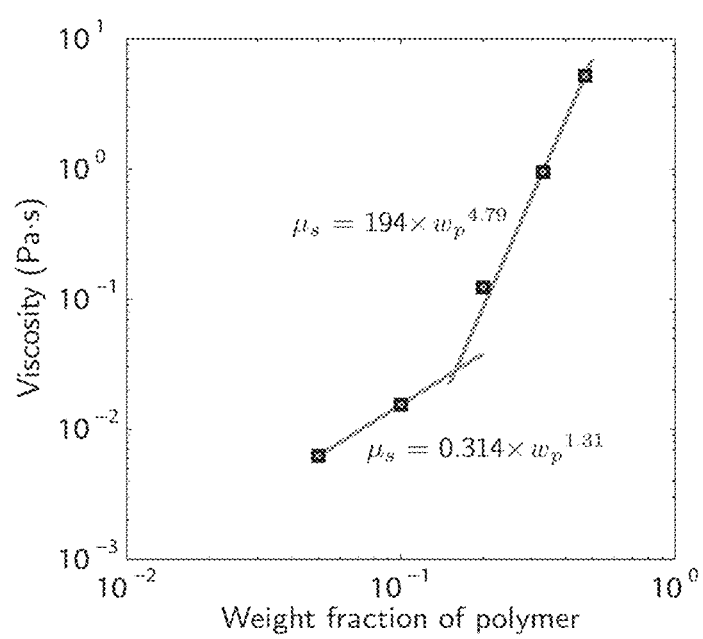
FIG. 24 presents the shear viscosity of water-excipient solutions versus weight fraction of the polymeric excipient (PEG 35k)

It was found that the shear viscosities of the PEG 35k-water solutions investigated were highly dependent on the weight fraction of polymer, $w_p$, in the measured range $0.05 < w_p < 0.47$. But the shear viscosity of a specific solution (e.g., a solution at a given weight fraction of the polymer) was mostly independent of shear rate $\dot{\gamma}$, if $1\text{ s}^{-1} < \dot{\gamma} < 100\text{ s}^{-1}$. In FIG. 24, an average of the viscosity measured in the given shear rate range is plotted versus the polymer weight fraction. At small weight fractions of the polymer (i.e. in the range $0.05 < w_p < 0.16$), the shear viscosity, $\mu_s$, follows roughly $\mu_s = 0.314 \times w_p^{1.31}$. As the weight fraction of polymer is increased beyond about 0.15, however, the curve of $\mu_s$ versus $w_p$ changes to a much stronger dependence on $w_p$. The viscosity roughly follows $\mu_s = 194 \times w_p^{4.79}$ if $0.16 < w_p < 0.47$.

From this data, both the microstructure and select properties of the polymer solution can be estimated. In an infinitely dilute water-polymer solution where the polymer molecules can be considered as individual units that do not touch as shown in FIG. 26a, according to the Einstein viscosity relation, the solution viscosity is a linear function of the polymer concentration, $c_p$. The experimental results suggest that the dilute solution approximations are valid in the range $0.05 < w_p < 0.16$.

In a dilute solution, the diffusivity, $D_p$, of a linear polymer (a relevant property for dosage form disintegration) in a θ-solvent follows Zimm's equation:

$$D_p = 0.192 \frac{k_b T}{N^{0.5} b \mu_l} \tag{17}$$

where $k_b$ is Boltzmann's constant, T the temperature, N the number of bonds of the polymeric chain, and b the bond length. Using T=310 K, N=2385, b=1.54 A, and $\mu_f$=0.001 Pa·s (as for the dilute PEG 35k-water solutions), $D_p$=1.09× $10^{-10}$ m²/s.

The dilute solution assumptions, however, break down if the concentration is increased to the value where the molecules touch. The critical polymer concentration, $c_p^*$, at which the polymer molecules entangle (another relevant property for dosage form disintegration) is about:

$$c_p^* \cong \frac{3M}{4\pi N_A R_g^3} = \frac{3M}{4\pi N_A} \left(\frac{\sqrt{6}}{N^\nu b}\right)^3 \tag{18}$$

where M is the molecular weight of the polymer and $N_A$ Avogadro's number. The experimental data presented in FIG. 24 suggest that $w_p^* \approx 0.16$ and $c_p^* \approx 163.4$ kg/m³. This result agrees with the value calculated by Eq. (18) if the parameter values given above are used and the Flory exponent $\nu$=0.55.

The solution is considered semi-dilute if the polymer concentration is above $c_p^*$. Typically, in the semi-dilute region $\mu_s \sim c_p^{4-6}$. This law is in agreement with our experiments in the range $0.16 < w_p < 0.47$.

Example 7: Viscosities of Kollicoat IR-Water Solutions

The shear viscosities of Kollicoat IR-physiological/body fluid solutions were determined by first mixing water with Kollicoat IR at polymer concentrations of 2.5, 5, 10, 15, 20, 25, 30, 35, and 40 wt %. A shear rheometer (TA Instruments, ARG2 Rheometer, stress-controlled) equipped with a 60 mm diameter cone with an apex angle of 178° was used. The temperature was 37° C. during the experiments, and the shear strain-rate range was $1\ s^{-1}$-$100\ s^{-1}$.

Figure 25:
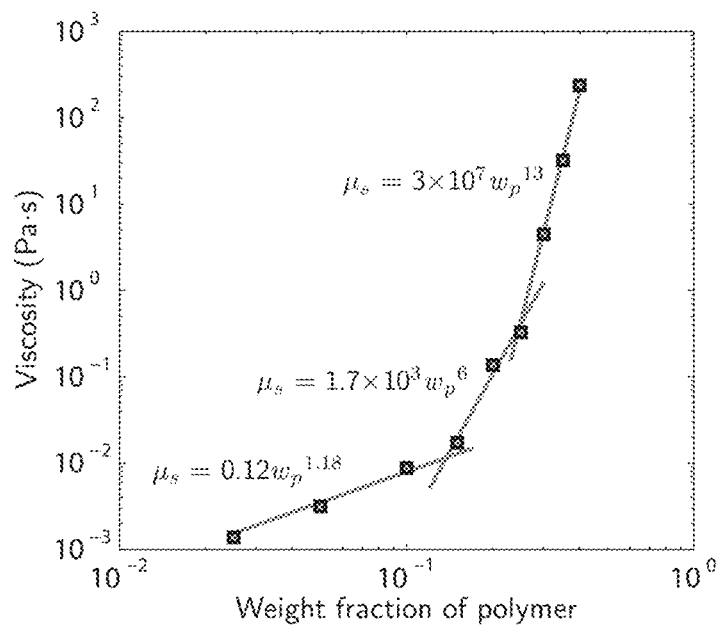
FIG. 25 shows the results of shear viscosity measurements of additional water-excipient solutions versus weight fraction of the polymeric excipient. Polyvinyl alcohol-polyethylene glycol graft copolymer 3:1 with a molecular weight of 45,000 Daltons (tradename: Kollicoat IR) was the excipient in this case.
Figure 26:
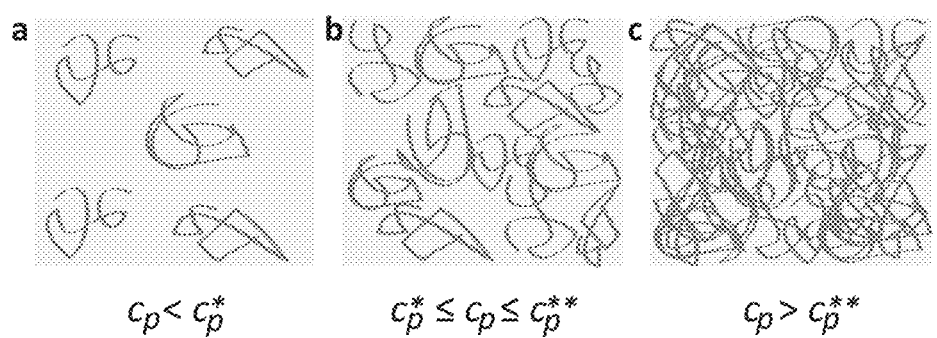
FIG. 26 presents schematics of polymer molecules solvated by a dissolution medium at a polymer concentration, $c_p$, of (a) $c_p < c_p^*$ (or $w_p < w_p^*$) (b) $c_p^* \leq c_p \leq c_p^{**}$ (or $w_p^* \leq w_p \leq w_p^{}$), and (c) $c_p > c_p^{}$ (or $w_p > w_p^{**}$).

FIG. 25 presents the viscosity versus weight fraction of polymer. At small weight fractions of the polymer (i.e. in the range $0.025 < w_p < 0.14$), the shear viscosity follows roughly $\mu_s = 0.12 \times w_p^{1.18}$. Then if $0.14 < w_p < 0.25$, the shear viscosity is about $\mu_s = 1.7 \times w_p^6$, a much stronger dependence on $w_p$. As the weight fraction of polymer is increased beyond 0.25, the curve of $\mu_s$ versus $w_p$ changes to an even stronger dependence on $w_p$. In the range $0.25 < w_p < 0.4$ the viscosity roughly follows $\mu_s = 3 \times 10^7\ w_p^{13}$.

These results allow us to estimate the structure of the water-polymer solutions. The viscosity of an infinitely dilute water-polymer solution is a linear function of the polymer concentration, and the results of this work suggest that the solution is dilute up to $w_p^* = 0.14$. In such a dilute solution, the polymer molecules are individual molecules surrounded by water. They do not touch each other or form an interconnected structure as shown in FIG. 26a.

Then in the semi-dilute region the solution viscosity typically follows $\mu_s \sim c_p^{4-6}$. This work suggests that the solution is semidilute if $0.14 < w_p < 0.25$. In such semidilute solutions, the polymer molecules touch, but entanglement of the chains of different molecules is minimal (FIG. 26b).

If the polymer concentration is increased beyond $w_p^{}$ (or $c_p^{}$) ($w_p^{**} \approx 0.25$ in the system of this example), however, the polymer molecules may entangle to fit in the given space (FIG. 26c). This results in stronger dependence of shear viscosity versus weight fraction of polymer. In the system of the present example, $\mu_s \sim w_p^{13}$ in this region. The solution is therefore concentrated. We may note that well within the concentrated region, at a polymer concentration of 0.35 or above, the material may behave like a semisolid.

Dosage Form Application Examples

In some embodiments, the amount of active ingredient contained in a dosage form disclosed in this invention is appropriate for administration in a therapeutic regimen that shows a statistically significant probability of achieving a predetermined therapeutic effect when administered to a relevant population. By way of example but not by way of limitation, active ingredients may be selected from the group consisting of acetaminophen, aspirin, caffeine, ibuprofen, an analgesic, an anti-inflammatory agent, an anthelmintic, antiarrhythmic, antibiotic, anticoagulant, antidepressant, antidiabetic, antiepileptic, antihistamine, antihypertensive, antimuscarinic, antimycobacterial, antineoplastic, immunosuppressant, antihyroid, antiviral, anxiolytic and sedatives, beta-adrenoceptor blocking agents, cardiac inotropic agent, corticosteroid, cough suppressant, diuretic, dopaminergic, immunological agent, lipid regulating agent, muscle relaxant, parasympathomimetic, parathyroid, calcitonin and biphosphonates, prostaglandin, radiopharmaceutical, anti-allergic agent, sympathomimetic, thyroid agent, PDE IV inhibitor, CSBP/RK/p38 inhibitor, or a vasodilator).

In conclusion, this invention discloses a dosage form with predictable structure and drug release behaviour. Both can be tailored by well-controllable parameters. This enables faster and more economical development and manufacture of pharmaceutical dosage forms, and higher quality and more personalized medical treatments.

It is contemplated that a particular feature described either individually or as part of an embodiment in this disclosure can be combined with other individually described features, or parts of other embodiments, even if the other features and embodiments make no mention of the particular feature. Thus, the invention herein extends to such specific combinations not already described. Furthermore, the drawings and embodiments of the invention herein have been presented as examples, and not as limitations. Thus, it is to be understood that the invention herein is not limited to these precise embodiments. Other embodiments apparent to those of ordinary skill in the art are within the scope of what is claimed.

We claim:

1. A pharmaceutical dosage form comprising:
   a drug-containing solid having an outer surface and an internal, three dimensional fiber network structure contiguous with and terminating at said outer surface;
   said three dimensional fiber network structure comprising one or more fibers with average fiber thickness in the range of 1.75 µm to 2.5 mm;
   said fibers having at least one active ingredient and at least one excipient through the fiber thickness, said excipient having a solubility in physiological fluid under physiological conditions greater than 1 g/l;
   said fibers further comprising at least one fiber segment bonded to another fiber segment at a point contact, the number of point contacts in the three dimensional fiber network structure being precisely controlled;
   said fibers further comprising fiber segments separated and spaced from adjoining fiber segments by free spacings, said free spacings defining at least an interconnected free space through the drug-containing solid; and
   said interconnected free space terminating at said outer surface and filled with at least a gas;
   wherein
   the average effective free spacing between fiber segments across an interconnected free space is in the range between 1 µm and 5 mm.

2. The dosage form of claim 1, wherein the one or more fibers comprise an average thickness in the range of 10 µm to 2 mm.

3. The dosage form of claim 1, wherein the free spacing between the fiber segments is so that the percolation time of physiological/body fluid into one or more interconnected free spaces of the dosage form is no greater than 900 seconds under physiological conditions.

4. The dosage form of claim 1, wherein the effective free spacing between the fiber segments across an interconnected free space on average is in the range of 10 µm to 4 mm.

5. The dosage form of claim 1, wherein a contact width between two fibers or two fiber segments is no greater than 2.5 mm.

6. The dosage form of claim 1, wherein at least one fiber segment is oriented parallel to a second fiber segment.

7. The dosage form of claim 1, wherein the spacing between adjacent fiber segments is precisely controlled.

8. The dosage form of claim 1, wherein the three dimensional fiber network structure comprises an ordered structure.

9. The dosage form of claim 1, wherein the inter-fiber spacing and fiber thickness are precisely controlled.

10. The dosage form of claim 1, wherein a volume fraction of the drug containing fibers with respect to a representative control volume of the dosage form is no greater than 0.98.

11. The dosage form of claim 1, wherein at least one excipient is wetted by a physiological/body fluid under physiological conditions.

12. The dosage form of claim 1, wherein at least one excipient is soluble in a physiological/body fluid and comprises a solubility greater than 5 g/l in said physiological/body fluid under physiological conditions.

13. The dosage form of claim 12, wherein dissolved molecules of the soluble excipient comprise a diffusivity greater than $1 \times 10^{-12}$ m$^2$/s in a physiological/body fluid under physiological conditions.

14. The dosage form of claim 1, wherein at least one excipient is absorptive of a physiological/body fluid, and wherein rate of penetration of the physiological/body fluid into a fiber or said absorptive excipient under physiological conditions is greater than the average fiber thickness divided by 3600 seconds.

15. The dosage form of claim 1, wherein at least one excipient is absorptive of a physiological/body fluid, and wherein an effective diffusivity of physiological/body fluid in a fiber or said absorptive excipient is greater than $0.5 \times 10^{-11}$ m$^2$/s under physiological conditions.

16. The dosage form of claim 1, wherein at least one excipient transitions from solid to a fluidic or gel consistency solution upon contact with a volume of physiological/body fluid equal to the volume of the one or more free spaces of the dosage form, said solution having a viscosity less than 500 Pa·s under physiological conditions.

17. The dosage form of claim 1, wherein at least one excipient is a polymer with molecular weight between 0.8 kg/mol and 2000 kg/mol.

18. The dosage form of claim 1, wherein at least one excipient is selected from the group comprising polyethylene glycol (PEG), polyethylene oxide, polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates, poly(methacrylic acid, ethyl acrylate) 1:1, butylmethacrylat-(2-dimethylaminoethyl)methacrylat-methylmathacrylat-copolymer, gelatin, cellulose, hydroxypropyl cellulose, hydroxyethyl cellulose, methyl cellulose, hydroxypropyl methyl ether cellulose, hydroxypropyl methylcellulose, starch, polylactide-co-glycolide, polyvinyl caprolactam-polyvinyl acetate-polyethylene glycol graft copolymer, lactose, pregelatinized starch, sodium starch glycolate, chitosan, pectin, polyols, lactitol, maltitol, mannitol, isomalt, acrylic acid crosslinked with allyl sucrose or allyl pentaerythritol, carbopol, and polyacrylic acid.

19. The dosage form of claim 1, wherein a free space is filled with a matter selected from the group comprising gas, liquid, or solid, or combinations thereof, and wherein said matter is partially or entirely removed upon contact with a physiological/body fluid under physiological conditions.

20. The dosage form of claim 19, wherein the gas comprises at least one of air, nitrogen, $CO_2$, argon, or oxygen.

21. The dosage form of claim 1, wherein the pharmaceutical dosage form has at least one dimension in the range of 1 mm to 30 mm.

22. The dosage form of claim 1, wherein the disintegration time of said dosage form is less than 45 minutes.

23. The dosage form of claim 1, wherein bonding between a fiber or fiber segment and another fiber or fiber segment is by interdiffusion of molecules between said fibers or fiber segments.

24. The dosage form of claim 1, wherein the one or more fibers comprise a single solid matrix through the fiber thickness.

25. The dosage form of claim 1, wherein plies of fibers, or fiber segments, are stacked in a cross-ply arrangement forming a three dimensional fiber network structure.

26. The dosage form of claim 1, wherein at least one fiber or at least one segment of a fiber is bonded to a second fiber or a second fiber segment to form an assembled structural element; said assembled structural element comprising one of (a) a zero-dimensional structural element, or (b) a one-dimensional structural element, or (c) a two-dimensional structural element; said assembled structural element further comprising an average thickness no greater than 2.5 mm.

27. The dosage form of claim 1, wherein at least one fiber or at least one segment of a fiber is aligned and bonded to a second fiber or a second fiber segment to form a wall.

28. The dosage form of claim 27, wherein less than twelve walls must be ruptured to obtain an interconnected cluster of free space from the outer surface of the drug-containing solid to any point in the internal structure, where the average wall thickness is in the range of 100 µm to 2 mm.

29. The dosage form of claim 27, wherein less than twenty four walls must be ruptured to obtain an interconnected cluster of free space from the outer surface of the drug-containing solid to any point in the internal structure, where the average wall thickness is smaller than 100 µm.

30. The dosage form of claim 1, wherein said dosage form has a coating covering its outer surface.

31. The dosage form of claim 1, wherein the three dimensional fiber network structure comprises a plurality of stacked layers of fibers or fiber segments, and wherein the standard deviation of the spacing between adjacent fiber segments in a layer is no greater than one sixth of the average value.

32. The dosage form of claim 1, wherein plies of fibers, or fiber segments, are stacked in a cross-ply arrangement forming a three dimensional fiber network structure, and wherein the inter-fiber spacing in a ply is precisely controlled having a standard deviation no greater than one sixth of the average value.

33. The dosage form of claim 1, wherein one or more excipients serve as fillers, stabilizers, preservatives, taste maskers, sweeteners, colorants, processing aids, or any other excipient functionality.

34. A pharmaceutical dosage form comprising:
a drug-containing solid having an outer surface and an internal, three dimensional fibrous network structure contiguous with and terminating at said outer surface;
said three dimensional fiber network structure comprising stacked layers of one or more fibers with average fiber thickness in the range of 5 µm to 2 mm;
said fibers comprising at least one active ingredient and at least one excipient through the fiber thickness, said excipient having a solubility in physiological fluid under physiological conditions greater than 1 g/l;
said fibers further comprising at least one fiber segment bonded to another fiber segment at a point contact;
said fibers further comprising fiber segments spaced from adjoining fiber segments by free spacings, said free spacings defining at least an interconnected free space through the drug-containing solid; and said interconnected free space terminating at said outer surface and filled with at least a gas; wherein the average effective free spacing between fiber segments across an interconnected free space is in the range between 1 μm and 5 mm.

35. A pharmaceutical dosage form comprising:

a drug-containing solid having an outer surface and an internal structure contiguous with and terminating at said outer surface;

said internal structure comprising a three dimensional structural network of one or more orderly arranged fibers, said fibers comprising a single solid matrix through the fiber thickness;

said fibers further comprising at least one active ingredient and at least one excipient through the fiber thickness, said excipient having a molecular weight in the rang of 0.8 kg/mol to 2000 k/mol and a solubility in physiological fluid under physiological conditions greater than 1 g/l;

said fibers further comprising at least one fiber segment bonded to another fiber segment by interdiffusion of molecules at a point contact, the number of point contacts in the three dimensional structural network of fibers being precisely controlled;

said fibers further comprising fiber segments spaced from adjoining fiber segments by free spacings, said free spacings defining at least an interconnected free space through the drug-containing solid; and said interconnected free space terminating at said outer surface and filled with at least a gas; wherein the average effective free spacing between fiber segments across an interconnected free space is in the range between 1 μm and 5 mm.

36. The dosage form of claim 34, wherein the three dimensional structural network of one or more fibers comprises at least three stacked layers of fibers or fiber segments.

37. The dosage form of claim 34, wherein bonding between a fiber or fiber segment and another fiber or fiber segment is by interdiffusion of molecules between said fibers or fiber segments.

38. The dosage form of claim 37, wherein the one or more fibers comprise a single solid matrix through the fiber thickness.

* * * * *